(12) United States Patent
Farag et al.

(10) Patent No.: US 8,360,986 B2
(45) Date of Patent: Jan. 29, 2013

(54) NON-CONTACT AND PASSIVE MEASUREMENT OF ARTERIAL PULSE THROUGH THERMAL IR IMAGING, AND ANALYSIS OF THERMAL IR IMAGERY

(75) Inventors: Aly A. Farag, Louisville, KY (US); Sergey Y. Chekmenev, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 1548 days.

(21) Appl. No.: 11/824,665

(22) Filed: Jul. 2, 2007

(65) Prior Publication Data

US 2008/0045847 A1    Feb. 21, 2008

Related U.S. Application Data

(60) Provisional application No. 60/817,819, filed on Jun. 30, 2006.

(51) Int. Cl.
*A61B 5/02* (2006.01)
(52) U.S. Cl. ........................................ 600/500; 600/502
(58) Field of Classification Search .................. 600/310, 600/481, 500, 504
See application file for complete search history.

(56) References Cited

PUBLICATIONS

S. Y. Chekmenev, A. A. Farag, and E. A. Essock. "Multiresolution approach for non-contact measurements of arterial pulse using thermal imaging." University of Louisville; Computer Vision and Pattern Recognition Workshop, 2006 Conference on Publication Jun. 17-22, 2006, pp. 129-137. ISBN: 0-7695-2646-2.*

N. Sun, M. Garbey, A. Merla and I. Pavlidis. "Imaging the cardiovascular pulse," Proceedings of the IEEE Computer Society Conference on Computer Vision and Pattern Recognition, San Diego, CA, Jun. 20-25, 2005.
P. J. Burt and E. Adelson, "The Laplacian pyramid as a compact image code," IEEE Trans. Commun., vol. COM-31, pp. 532-540, Apr. 1983.
Y. Atamaz and F. Govsa. "Anatomy of the superficial temporal artery and its branches: its importance for surgery." Surgical and Radiologic Anatomy, 28(3):248-253, 2004.
S. Mallat, "A wavelet tour of signal processing." Ecole Polytechniue, Paris, Courant Institute, New York University, A Harcourt Science and Technology Company, 2nd edition, pp. 188-197, 2001.
S. Mallat, "A Theory for Multiresolution Signal Decomposition: The Wavelet Representation," IEEE Transactions on Pattern Analysis and Machine Intelligence, vol. 11, No. 7, pp. 674-693, 1989.
F. Pompei and M. Pompeia. "Non-invasive temporal artery thermometry: Physics, physiology, and clinical accuracy." Medical Thermometry for SARS Detection, SPIE Defense and Security Symposium, Apr. 12-14, 2004, Orlando, FL.

(Continued)

*Primary Examiner* — Patricia Mallari
*Assistant Examiner* — Michael D'Angelo
(74) *Attorney, Agent, or Firm* — Greer, Burns & Crain Ltd.

(57) ABSTRACT

A non-contact, passive method for measurement of arterial pulse from areas such as the major superficial arteries of the body through analysis of thermal IR images acquired by passive thermal IR imaging sensors, and through the modeling of the pulsatile nature of the blood flow and arterial pulse propagation in the circulatory system. The method is automatic and does not need operator input. The output waveform readily contains the information on heart rate, cardiac interbeat intervals, heart-rate variability and other features inherent in arterial pulse. The potential applications of this method, device and system are in the fields of non-contact and passive measuring cardiovascular and autonomic regulatory functions, mental and emotional loads, assessment of health in general, prediction of ill physiological and mental conditions, smart rooms, human-computer interaction, polygraph testing, intent identification, and any other fields where non-contact, passive monitoring of heart-rate and its variability is needed.

21 Claims, 23 Drawing Sheets

PUBLICATIONS

N. Sun, M. Garbey, A. Merla, and I. Pavlidis. "Estimation of blood flow speed and vessel location from thermal video." IEEE Computer Society Conference on Computer Vision and Pattern Recognition, vol. l, Washington D.C., Jun. 27Jul. 2, 2004, pp. 356-363.

R. Murthy and I. Pavlidis, "Non-Contact Monitoring of Breathing Function Using Infrared Imaging," Department of Computer Science, University of Houston, http://www.cs.uh.edu, Technical Report No. US-CS-05-09, Apr. 9, 2005, pp. 1-17.

Kittler, J., Hatef, M., Duin, R.P.W., and Matas, J., "On Combining Classifiers", IEEE Transactions on Pattern Analysis and Machine Intellegence, vol. 20, No. 3., pp. 226-239, 1998.

Y. Freund and R.E. Schapire, "A decision—theoretic generalization of online learning and an application to boosting," Computational Learning Theory (Eurocolt), 1995.

Kinsner, W., "Is entropy suitable to characterize data and signals for cognitive informatics?" Cognitive Informatics, 2004. Proceedings of the Third IEEE International Conference on Aug. 16-17, 2004 pp. 6-21.

Chekmenev, S. Yu, et al., "Non-contact, Wavelet-based Measurement of Vital Signs using Thermal Imaging", *GVIP*, Dec. 19, 2005.

Chekmenev, Sergey Y., et al., "Multiresolution Approach for Noncontact Measurements of Arterial Pulse Using Thermal Imaging," R. Hammond, Ed, *Augmented Vision Perception in Infrared*, Chapter 4, pp. 87-112, Springer-Verlag, Berlin, Dec. 2008.

Chekmenev, Sergey Y., et al., "Thermal Imaging of the Superficial Temporal Artery: An Arterial Pulse Recovery Mode," *Proc. of 3rd IEEE International Workshop on Object Tracking and Classification in and Beyond the Visible Spectrum (OTCBVS'07)*, Minneaplois, MN, USA, Jun. 22, 2007, pp. 1-8.

* cited by examiner

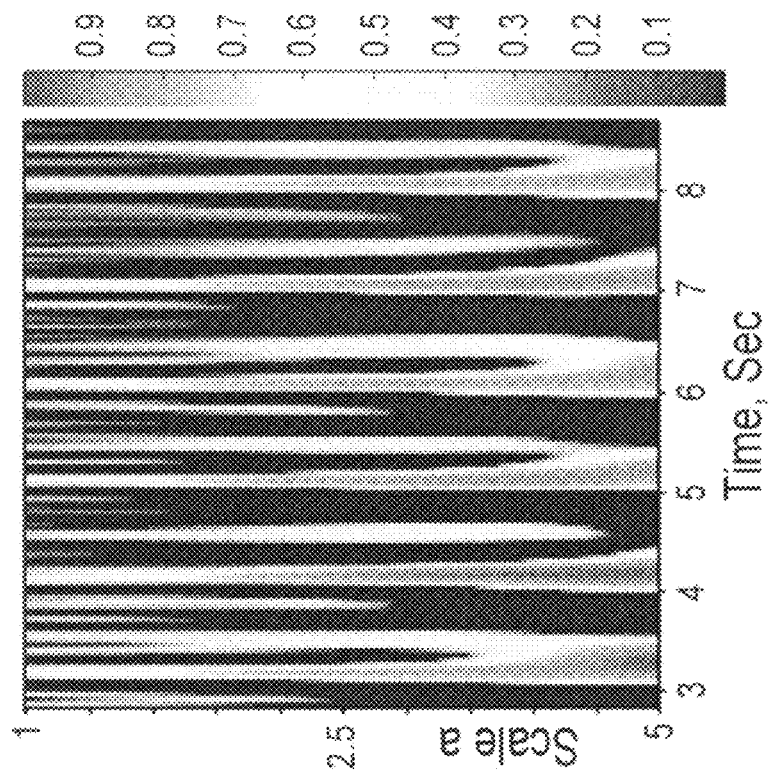
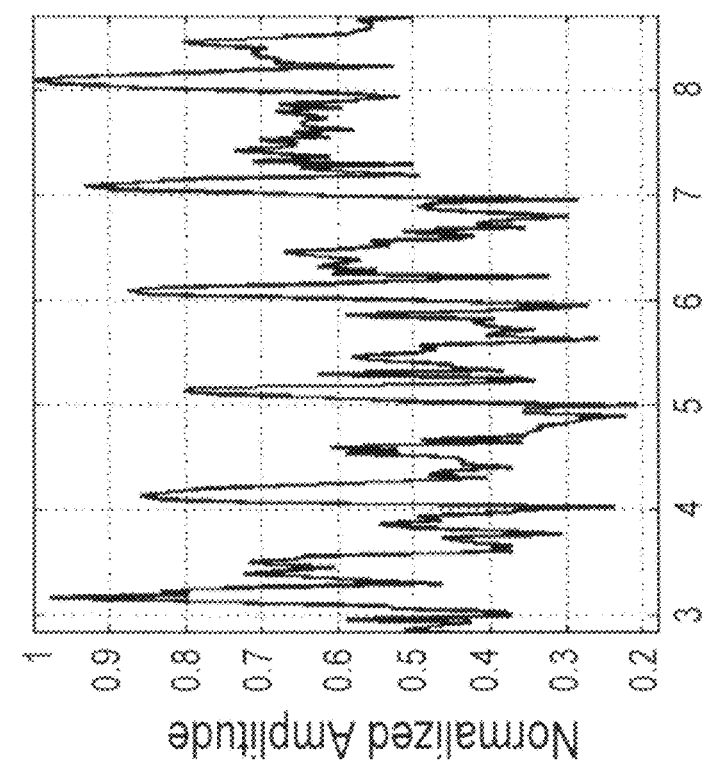
Figure 15(B)
Figure 15(A)

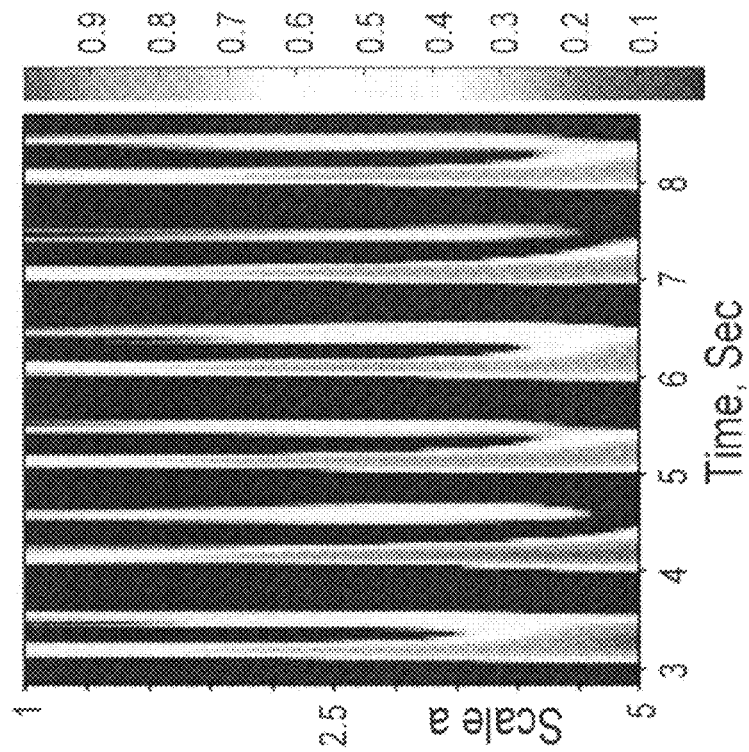
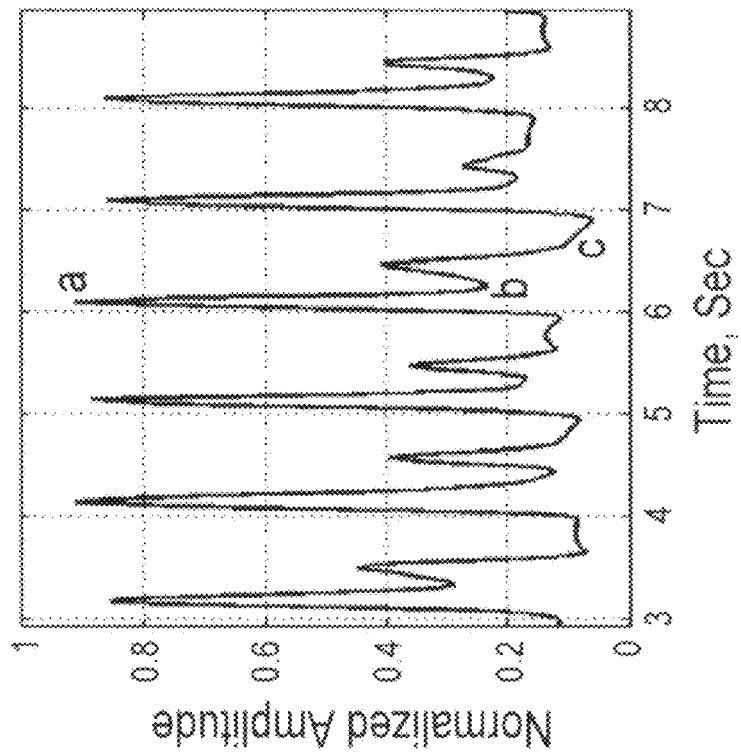
Figure 16(B)
Figure 16(A)

NON-CONTACT AND PASSIVE MEASUREMENT OF ARTERIAL PULSE THROUGH THERMAL IR IMAGING, AND ANALYSIS OF THERMAL IR IMAGERY

CLAIM FOR PRIORITY AND REFERENCE TO RELATED APPLICATION

This application claims priority under 35 U.S.C. §119 from prior provisional application Ser. No. 60/817,819, filed Jun. 30, 2006.

FIELD OF THE INVENTION

One broad field of the invention is medical devices, and more particularly medical devices related to determining pulse waveforms, such as determining, in a non-contact method, arterial pulse waveforms from major superficial arteries of the body. Another field of the invention is image and signal analysis.

BACKGROUND

Information concerning cardiac and autonomic functions is critical for heart diagnostics and diagnostics of autonomous nervous system, as well as for other medical diagnostics. Accurate monitoring of heart rate and heart rate variability in both time and frequency domains is essential for measuring cardiovascular and autonomic regulatory functions, mental and emotional loads, prediction of dangerous health conditions such as approaching heart attack, stroke and for assessment of health in general.

The arterial blood pressure wave is created during the ventricular systole, and propagates along the arterial tree pumping the blood in the circulatory system. Propagating along the arterial network, the pressure wave causes the distention of arterial walls which can be palpated as an arterial pulse from the major superficial arteries of the body. Doppler ultrasound, arterial tonometry and oximetry are traditional approaches to track the hemodynamics changes in the arteries. Arterial pulse, in most cases, can provide an accurate measure of heart rate and its variability, and can be measured at any point on the body near major superficial arteries. Superficial arteries are found, for example, near the wrist (radial artery), neck (carotid artery), ear (temporal artery), elbow (brachial artery), and groin (femoral artery).

Some devices that measure heart rate, heart rate variability and heart functions use electrodes, or clips, that are placed in contact with the skin. An electrocardiogram (ECG or EKG), which is produced by an electrocardiograph, is commonly used in clinical situations, including critical care, to show heart rate and its variability. The function produced over time, or in the frequency domain, can reveal information that can be useful to medical practitioners when diagnosing diseases. However, placement of the electrodes with the required body contact can be inconvenient, and can slow the acquisition of important data. The use of contact devices, though non-contact, for monitoring the heart condition is undesirable in prolonged monitoring and studies. Moreover, in some applications like magnetic resonance imaging (in which exact event of heart contraction needs to be known to remove the motion artifact on an MRI image due to the heart beat by itself) the use of electrodes disturbs the measurements of the heart rate waveforms because of the strong electromagnetic field.

Various methods have been proposed to access heart performance by measuring blood circulation, such as methods using Doppler Ultrasound, Radar, Laser Vibrometer, Oximetry and Arterial Tonometry. The Doppler, Radar and Laser devices have the disadvantage of relying on active sensors, that is, energy is directed at the body while obtaining the measurements, which energy may have harmful side effects on the health of the individual. Focusing the energy on a proper body parts could also be an issue. Arterial Tonometry and oximetry are contact measurement methods, which, like other contact measurement methods, are somewhat intrusive, require significant subject cooperation and are not favorable in a prolonged continuous monitoring or surveillance application.

Others have proposed to address these problems with non-contact passive methods of obtaining heart function data through the use of imaging. For example, a research group run by Dr. Ioannis Pavlidis at the University of Houston has proposed an image-based technique in which mid-wave Infra-Red (IR) sensors are used to measure cardiac pulse at a distance, by sensing the tissue temperature profile along the superficial blood vessels. See N. Sun, M. Garbey, A. Merla and I. Pavlidis, "Imaging the Cardiovascular Pulse," Proceedings of the IEEE Computer Society Conference on Computer Vision and Pattern Recognition, San Diego, Cailf., Jun. 20-25, 2005 (hereinafter "Pavlidis et al."). In this method, a longitudinal linear branch of a superficial blood vessel is manually selected through a graphic user interface and the heartbeat frequency is recovered in the frequency domain by filtering the unwanted artifact frequency peaks. A two to three minute time lapse is used to estimate the heart beat rate by monitoring the manually preselected region along the vessel (a vein). The output is the estimated pulse during the time lapse. However, this method has some limitations, such that only the dominant heart rate frequency is reported, not the actual heart rate waveform, so the valuable interbeat pulse to pulse information and the heart rate variability (i.e., the beat to beat variations) are not determined. The heart beat never stays the same, even within the stated two to three minute intervals. This is why the heart rate variability comes into play. Pulse to pulse variation is itself an important vital sign for indicating the cardiovascular function, autonomic function and physical functioning level. For example, heart rate recovery, such as measured after the first minute after exercise, is a powerful predictor of overall mortality, independent of workload. In elderly or disabled care, a person could pass away during the two to three minute interval before the warning system would inform the nurse. This makes approaches designed for estimation of time averaged heart rate statistics for such long intervals like two to three minutes like in the Pavlidis et. al. method to be impractical for certain situations. Further, due to the analysis methods used, only heart rates between the range of 40-100 beats per minute (bpm) can be reported in the Pavlidis et. al approach. This limitation of the Pavlidis et al. approach prevents detection of certain problems, such as an arterial blockage, during which the heart rate may suddenly increase up to three hundred beats per minute. Finally, this method also has the disadvantage that it requires a medical expert or other highly trained person to manually select the region on the skin to be measured.

While estimated pulse provides useful information, more data concerning heart function is important for many types of diagnoses. Further, minimal invasiveness and speed of data acquisition are also important. Additionally, it is desirable to minimize operator involvement and possible error.

SUMMARY

The invention provides an automated imaging device, method and system for determining a waveform of heart function that can be used for many diagnostic purposes. The device of the invention is non-invasive, non-contact and passive, and automatically obtains the necessary data from an image of the skin taken near a superficial artery.

More specifically, embodiments of the invention provide a non-contact and passive method for measurement of the arterial pulse from areas such as the major superficial arteries of the body through analysis of thermal IR images acquired by passive thermal IR imaging sensors, and through the modeling of the pulsatile nature of the blood flow and arterial pulse propagation in the circulatory system. The method is automatic and does not need operator input. The output waveform readily contains the information on heart rate, cardiac interbeat intervals, heart-rate variability and other features inherent in arterial pulse. The potential applications of this method, device and system are in the fields of non-contact and passive measuring cardiovascular and autonomic regulatory functions, mental and emotional loads, assessment of health in general, prediction of ill physiological and mental conditions, smart rooms, human-computer interaction, polygraph testing, intent identification, and any other fields where non-contact, passive monitoring of heart-rate and its variability is needed.

More specifically, one embodiment of the invention relates to a method for measuring of arterial pulse that includes the steps of obtaining a sequence of thermal infrared images from a subject, wherein each thermal infrared image is obtained without skin contact with the subject; performing a first analysis of the sequence of obtained thermal infrared images to detect at least one region of interest for further analysis; performing a second analysis of the sequence of obtained thermal infrared images to track the at least one region of interest, wherein the second analysis includes detecting a corresponding spatial location of each region of interest; performing a third analysis of the at least one region of interest to select at least one configuration of a region of measurement of arterial pulse within the corresponding region of interest; and determining at least one arterial pulse waveform from the selected configuration of region of measurement. In some embodiments, the first analysis includes automatic selection of a pixel area using multiscale image decomposition and multiresolution analysis.

BRIEF DESCRIPTION OF THE DRAWINGS

Preferred embodiments of the present invention are described herein with reference to the drawings wherein:

FIG. 15(A) is a six second segment of an arterial pulse waveform;

FIG. 15(B) is a continuous wavelet transform (CWT) of FIG. 12(A);

FIG. 16(A) is a reconstructed six second segment of the arterial pulse waveform from a carotid artery (where "a" is a systolic peak pressure, "b" is a dicrotic notch, and "c" is the end diastolic pressure);

FIG. 16(B) is a continuous wavelet transform (CWT) of FIG. 13(A);

DETAILED DESCRIPTION OF THE PREFERRED EMBODIMENTS OF THE INVENTION

Figure 1:
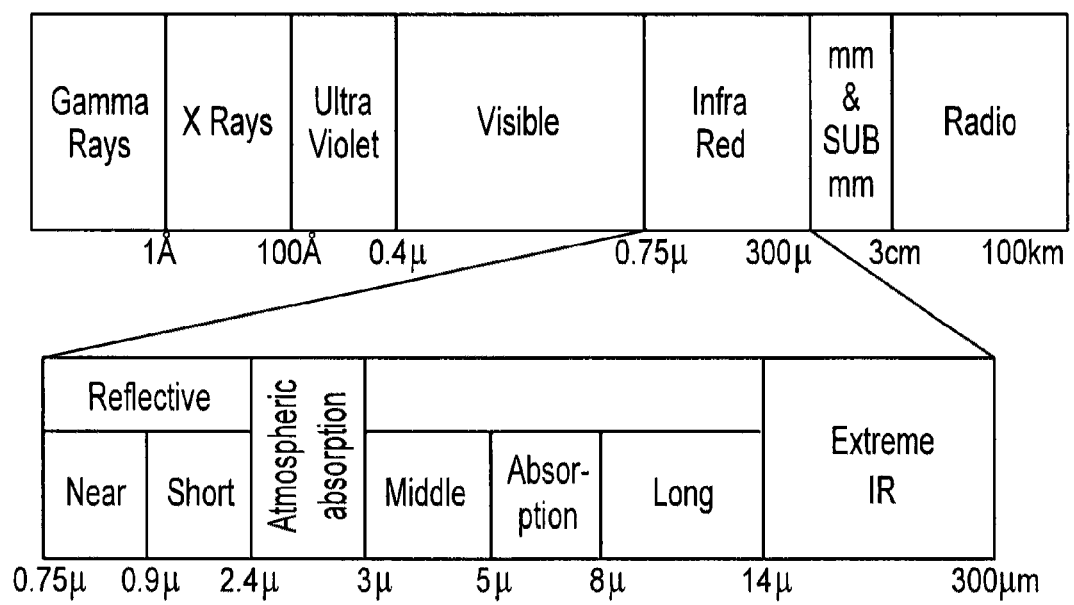
FIG. 1 is an explanatory view of the electromagnetic (EM) spectrum.

Embodiments of the present invention provide a non-contact and passive methodology for accurate measurement of the arterial pulse by thermal IR (Infra-Red) imaging of the superficial arteries of the human body. Preferred embodiments of the present invention measure the events of pulse propagation through a superficial artery through the measurement of heat variations on the skin surrounding the artery.

A preferred embodiment of a device of the invention measures an arterial pulse waveform from the thermal radiation emitted naturally, with no artificial illumination by the skin of a subject, e.g., a human patient. Devices of the invention can make measurements in an area of skin that is near major superficial arteries. An example of a device of the invention uses a thermal infrared (IR) camera sensor, such as an thermal IR camera. The thermal IR imaging sensor is capable to detect pulsating thermal patterns on the surface of the skin produced by propagating arterial pulse waves through out a superficial artery. A multiresolution processing of acquired thermal IR images and processing of arterial pulse thermal signatures using the wavelet analysis framework is conducted by a controller, e.g., computer software, that extracts a waveform of the heart function from the data.

Devices of the invention are passive, and do not emit energy into the subject. Devices of the invention do not require the attachment of any equipment onto a subject. With devices of the invention, the region of arterial pulse measurement on the skin surrounding the artery is automatically detected, reducing the potential for errors that can result from improper use of other measurement devices. In addition, methods, devices and systems of the invention provide detailed heart function data, specifically a time varying arterial pulse thermal waveform that in particular contains information on heart rate, beat-to-beat intervals and heart rate variability.

Preferred embodiments of devices of the invention make use of an important property recognized by the inventors, namely that that the arterial wall volumetric response to a pressure variation distorts the heat distribution along the artery. The inventors further recognized that these distortions are more pronounced in the radial direction, the direction perpendicular to the direction of arterial blood pressure wave propagation within the artery. The areas in the vicinity of the artery, where the heat redistribution due to the pulse propagation is most pronounced, are automatically detected using the quasi-periodic nature of the arterial pulse and the proposed multiresolution and wavelet based pulse recovery algorithms. The arterial pulse signal is recovered in the time domain featured similarly to the contact medical devices designed to measure the peripheral arterial pulse (such as the oximetry sensor). The use of multiresolution theory and continuous wavelet analysis allows to separate the irrelevant heat variations from those produced by the pulse propagation events and substantially suppress severe thermal noise. Specifically designed algorithms based on the multiresolution analysis of thermal images and continuous wavelet analysis of pulse measurements from various ROM configurations permit real-time computation of a descriptive arterial pulse waveform, instead of estimating just the dominant heart rate frequency during the lengthy time interval. Arterial pulse peaks can be directly observed from the measured waveform, meaning that no particular time needs to be specified for the arterial pulse measurement (heartbeat estimation). The inter-beat time interval can be directly extracted from the waveforms and used in various applications in both time and frequency domains.

According to the embodiments of the invention, the quasi-periodic thermal pattern produced by an artery can be measured on the skin in the vicinity of the superficial arteries. The location of the skin measurement patches can be automatically detected on the skin surrounding the artery of interest. Estimation of heart beat can be done in time domain, permitting the real time visualization of the arterial pulse waveform and estimation of the beat-to-beat time intervals and its variability.

Accurate tracking of the skin in thermal IR can be achieved with the use of the features extracted from edge representation. The brightness or the thermal pattern of the skin in thermal IR band varies substantially with time due to numerous heat phenomena. However, the overall edge representation is relatively stable. The multiresolution features (edge oriented histograms for example) based on such representation are robust enough to accurately track the region of interest over the time. Important cardiovascular indexes, such as the location of systolic blood pressure peaks, left ventricular blood injection time and the rate of change of blood pressure (slope of the systolic blood pressure upstroke) can be estimated from the arterial pulse waveforms measured from the major superficial arteries of the body. Measurements are adequate for non-contact vital sign monitoring from variable distances.

The present invention can also be used to provide an additional important diagnostic tool. Heart beat is an important indicator of a living person and their physical functioning level. Normal ranges of cardiac pulse vary with age, sex, weight, exercise tolerance and body conditions. A delayed heart rate recovery, for example, after the first minute after exercise, is a powerful predictor of overall mortality, independent of workload. This vital sign may indicate an approaching heart attack, mental and physical stress and many other dangerous conditions. In healthcare the monitoring of heart rate and heart rate variability is essential for measuring cardiovascular and autonomic regulatory functions, mental and emotional loads, and for assessment of health in general. Accurate and automatic measurement of this vital index at a distance, non-intrusively using passive sensors, provides a significant contribution to the fields of non-contact health state/physiology monitoring, smart rooms, polygraph testing, and intent identification. Such monitoring of human psychology can also add an additional layer of biometrics for remote detection of threats and intents in modern surveillance systems as well.

Turning now to the figures, embodiments of the invention will now be described in more detail. In one preferred embodiment, the thermal Infra-Red (IR) band of the electromagnetic (EM) spectrum is utilized for imaging of the readily accessible arteries, such as those found in the neck and face. As shown in FIG. 1, the IR band is typically divided into a reflective band (0.75-3 µm), a thermal band (3-14 µm) and an extreme band (14-300 µm). The reflective and thermal bands are further sub-divided into the following: Near Wave IR (NWIR: 0.75-2.4 µm), Short Wave IR (SWIR: 0.9-2.4 µm), Middle Wave IR (MWIR: 3-5 µm), Long Wave IR (LWIR: 8-14 µm).

The actual radiation rate at a particular wavelength depends on both the object's temperature and its emissivity. Human skin is almost a perfect black body (i.e., a perfect emitter/absorber of thermal energy) having an emissivity value of 0.98, regardless of race and skin color. The wavelength power distribution radiated by a black body is given by Planck's radiation law (Equation (1)):

$$P_\lambda = \frac{2\pi hc^2}{\lambda^5 [\exp(hc/\lambda KT - 1]} \tag{1}$$

where $P_\lambda$ is Power (W/m$^2$) emitted at particular wavelength $\lambda$ (m), h is Planck's constant ($6.626 \times 10^{-34}$ Js), c is the speed of light ($3 \times 10^8$ m/s), K is Boltzmann's constant ($1.38 \times 10^{-23}$ J/K), and T is Temperature (K).

Figure 2:
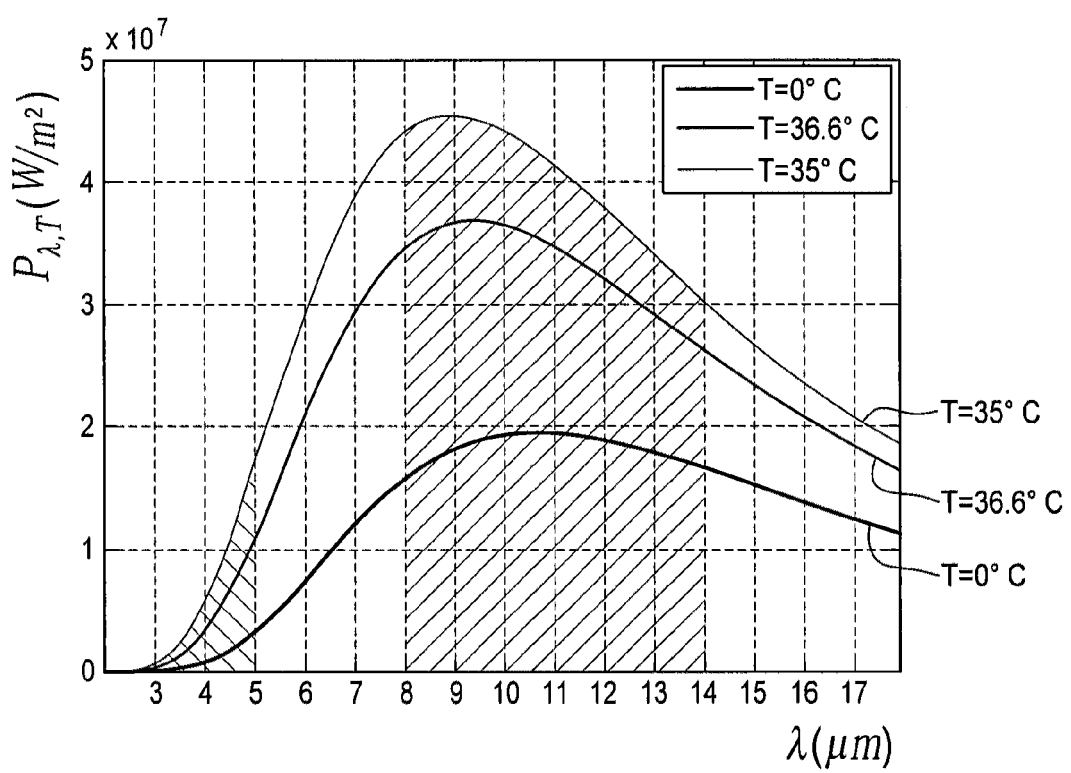
FIG. 2 is a spectral power distribution graph.

The distribution of energy across the MWIR and LWIR at three different temperatures (0° C., 36.6° C., and 50° C.) is illustrated in FIG. 2. The total energy emitted per meter squared per second is the area under the Planck energy distribution curve. One observation that can be made from FIG. 2 is that the emission of energy at temperatures around the temperature of the human body (36.6° C.) is much higher within the LWIR band (8 µm-14 µm) than it is across the MWIR band (3 µm-5 µm). This increases the sensitivity but lowers the thermal contrast. In practice, both MWIR and LWIR are good candidates for biomedical applications. However there are some important differences between imaging in these bands. The MWIR band is significantly more susceptible to the ambient illumination than the LWIR band. This means that measurements in LWIR are inherently less affected by ambient illumination of hot objects like the sun, bulbs, fire, etc. This makes the LWIR more advantageous for measurements of the pulsatile heat patterns of human vital signs. The strength of the MWIR band lies in its lower optical diffraction and lower background radiation than that in LWIR, which actually results in sharper and more contrast imaging. Accordingly, the preferred embodiment utilizes the LWIR band for imaging the arterial pulse. However, given the proper circumstances, other bands could also be utilized, as well as using a range of wavelengths across multiple bands.

Heart rate is defined as the number of contractions of the heart in one minute, and is traditionally measured in beats per minute (bpm). The contractions produce sequential changes in pressure and blood flow in the heart chambers and blood vessels. These sequential blood pressure waves can be felt as an arterial pulse in peripheral arteries of the body. The pulse wave is more pronounced in the arteries, but gradually diminishes in the peripheral blood vessels until it cannot be felt in the venous network that returns blood to the heart.

Figure 3A:
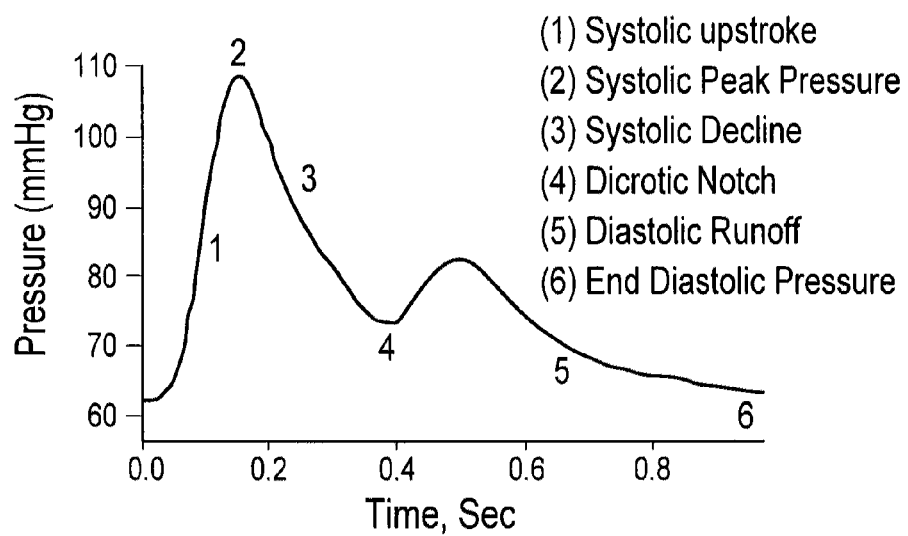
FIG. 3(A) is an arterial pressure waveform.
Figure 3B:
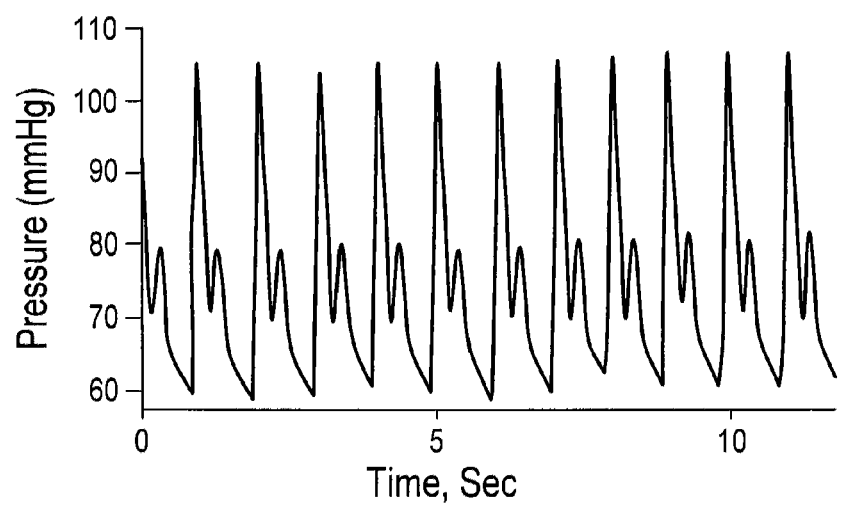
FIG. 3(B) is a sequence of arterial pulses measured with a Colin tonometer.

FIG. 3(A) shows an example of an arterial pulse curve. The systolic upstroke 1 (ascending limb) on this curve represents the rapid increase in arterial pressures and flows due to opening of the aortic and pulmonary valves during the ventricular systole. The maximum sharp peak 2 at the end of the ascending limb is the systolic peak pressure. The dicrotic notch 4 located on the systolic decline 3 is caused by the closure of the aortic valve during early diastole. The pressure then gradually drops during diastolic runoff 5 until the end-diastolic pressure 6. FIG. 3(B) shows a sequence of cardiac beats measured with a Colin tonometer from the carotid artery. The shape and the speed of the arterial pulse wave changes when it propagates along the arterial tree. This is mainly because of the change in mechanical properties of arterial walls (elastic tapering), and the decrease of the cross-sectional areas of the arteries (geometric tapering).

Various multiscale decomposition (MSD) schemes are proposed for multiresolution image analysis. Most popular are the Pyramid structures (such as Laplacian and Gaussian pyramids, Gradient Pyramids, Ratio-of-Low Pass Pyramids etc.) and the wavelet decomposition models. In one of the preferred embodiments of the present invention, a multiresolution (MR) analysis framework is utilized, such as the analysis framework disclosed in the following publications: S. Mallat, "A Compact Multiresolution Representation The Wavelet Model," Proc. IEEE Computer Society Workshop of Computer Vision, IEEE Computer Society Press, Washington D.C., pp. 2-7, 1987 and P. J. Burt & E. Adelson, "The Laplacian Pyramid As A Compact Image Model," IEEE Trans. Commun., vol. COM-31, pp. 532-540, April 1983, which is hereby incorporated by reference.

Using this framework, thermal IR images are represented and analyzed as a set of images of different scales (fine-to-coarse). This MSD allows for the selection of those scales that contain most of the heat information relevant to the true arterial pulse, with as minimal of a contribution as possible of other irrelevant heat patterns. In one preferred embodiment, the MSD is constructed by computing similarity measures between the LWIR images and a set of Mexican Hat (MH) wavelet kernels, at different scales and locations, as indicated by Equation (2):

$$MH(t) = (2-t)*e^{-\frac{1}{2}t} \quad t = \frac{(x-b_x)^2 + (y-b_y)^2}{a^2} \quad (2)$$

where $(b_x, b_y)$ is a translation vector, and a is a scale. This new fine-to-coarse representation allows the local temperature structures of the thermal IR images to be more clearly seen at different scales/wavelet bands by getting a strong response when the image pattern looks more like the analyzing convolution filter and a weak response when they are different. It should be understood that the MSD is not limited to the use of a particular analyzing kernel function. The MSD can be performed with the use of various kernels and various decomposition schemes. Such as for example in latest publication of the inventors: Sergey Y. Chekmenev, Aly A. Farag and Edward A. Essock, "Thermal Imaging of the Superficial Temporal Artery: An Arterial Pulse Recovery Model," IEEE International Workshop On Object Tracking and Classification Beyond the Visible Spectrum, PP. 1-6, Minneapolis, Minn., June 2007, which is hereby incorporated by reference, in which the MSD was performed using the orthogonal 2D directional Haar wavelet functions. It was demonstrated that the use of directional wavelet functions can better isolate the directional redistribution of heat due to the pulse propagation.

Figures 4A, 4B, 4C, 4D:
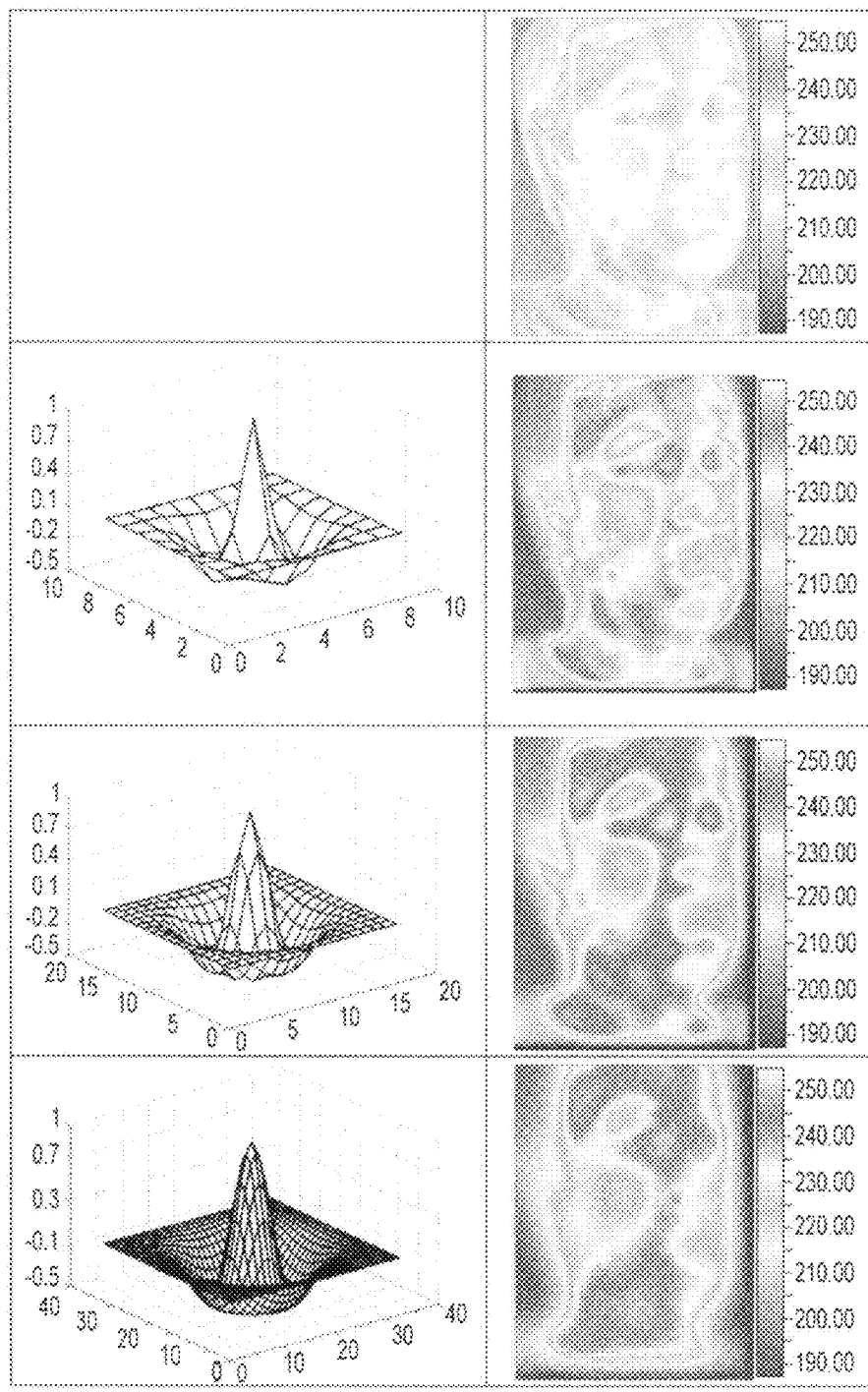
FIGS. 4(A)-4(D) show, from top to bottom, an original normalized thermogram image with no filtering; and then three different scale decompositions using Mexican Hat (MH) wavelet kernels (Note: other filters, such as Gabor, can also be successfully applied.)

FIGS. 4(A)-4(D) illustrate the thermal image decomposition using Mexican Hat kernels (Laplacian of the 2 dimensional Gauss function) at three different scales, where, FIG. 4(A) is the original, normalized thermogram image with no filtering; FIG. 4(B) is at a first scale; FIG. 4(C) is at a second scale and FIG. 4(D) is at a third scale. In this example, the successive size of each filter is doubled when going from the first scale to the second scale and from the second to the third scale. However, the use of other different multiscale decomposition schemes, types of filters and sizes is also contemplated. This sample use of Mexican Hat filters in FIGS. 4(A)-4(D) gives an idea how they can be applied for feature detection of regions of interest. In the figures, the 2D isotropic Mexican Hat filters of different scales are convolved with thermal IR image of the human face. The regions which look more like the analyzing kernel functions produce a stronger (brighter) response at various locations and scales. The temporal and carotid regions produce very prominent responses at various scales with respect to other structures of the face and neck. This example gives a clear idea of how the detection of superficial arteries in both scale and space domains can be implemented using MSD, the multiscale analysis with kernel functions which match/represent the applying features of blood vessel structures.

Figure 5:
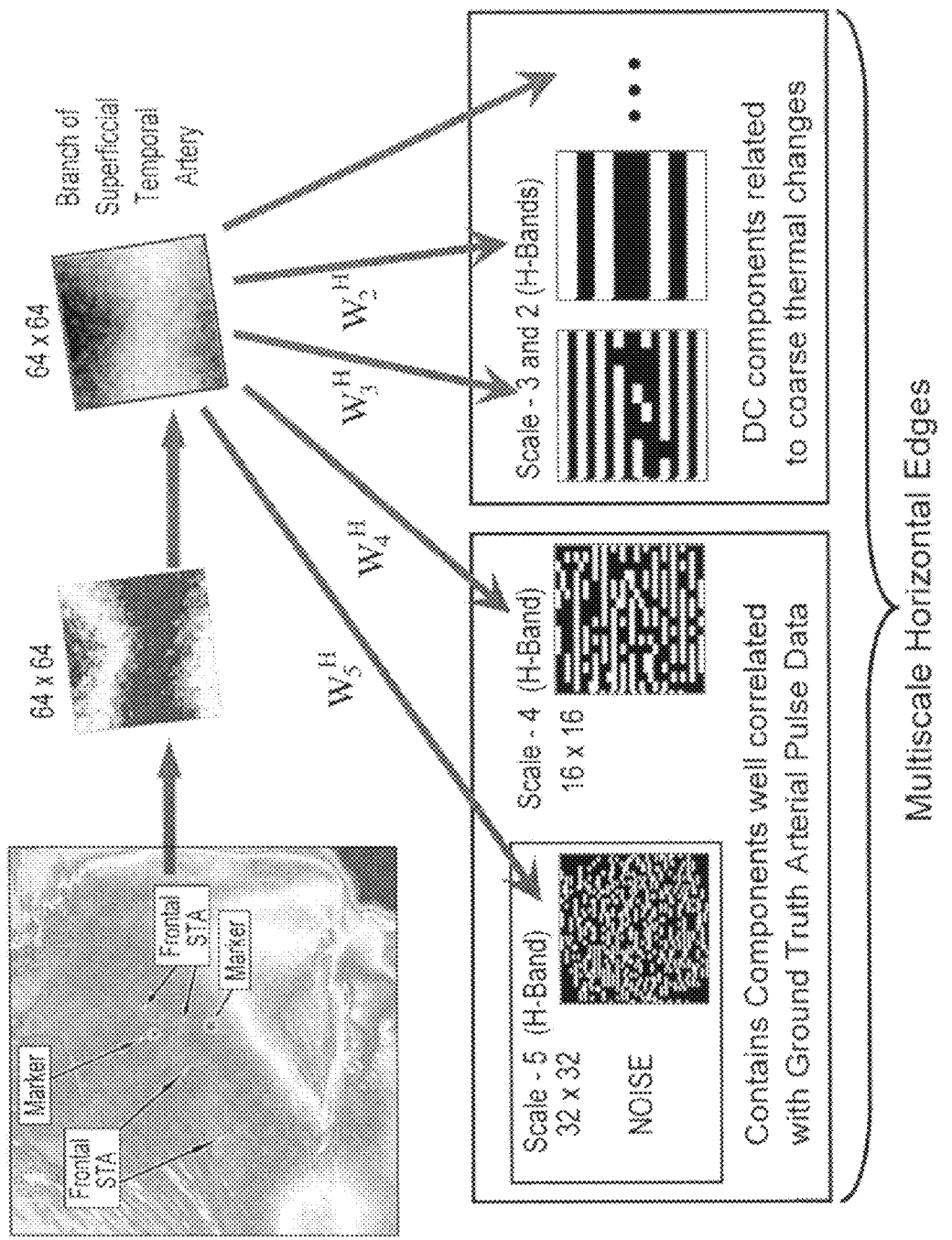
FIG. 5 illustrates multiscale decomposition (MSD) using the Mallat wavelet framework and 2D directional Haar wavelet filters in which the multiscale decomposition at wavelets bands that encode the horizontal edges along the branch of superficial temporal artery are illustrated.

FIG. 5 explains the idea of the usage of the directional wavelet functions in MSD for arterial pulse measurements. A 64 by 64 pixels patch of the superficial temporal artery is illustrated in the top of FIG. 5. The patch is rotated such as to be in parallel with the direction of the horizontal edge sensitive wavelets which capture the intensity variation along the columns. The multiscale horizontal wavelet bands of the patch are displayed in the bottom of FIG. 5. According to the experimental results the horizontal edge variations at scale-4 contain the components that are well correlated with the ground truth arterial pulse data. The H-data at scale-5 illustrated in the figure just in few cases yields a good match with ground truth measurements. However in most cases, this scale is dramatically affected by the high frequency noise, making the measurements produce inaccurate results. Lower scales such as scale-3 and scale-2 relate to very coarse representation of the STA branch. The variations at these scales reflect the arterial pulse propagation events very poorly, and are therefore not of the interest.

One of the important ideas behind the measurements of the arterial pulse in the present invention is the decomposition and analysis of thermal images at a set of fine to coarse scales. The goal of MSD is to identify the decomposition sub-bands at which the pulse propagation effect is the most pronounced whereas the influence of irrelevant noisy heat patterns is minimal. FIG. 6 illustrates the raw thermal images of the frontal branch of the superficial temporal artery. The images are displayed as three dimensional thermal maps. The X and Y are the spacial axes and the Z is the axis corresponding to the normalized temperature. From this figure it can be seen that the heavy noise is comparable to approximately ¼ of the DC thermal difference between the artery and the surrounding tissue in the data acquisition system used. According to findings of the inventors, the direct measurements of the arterial pulse from the raw thermal data was impossible, at least in the lab settings where the experiments were performed. To remedy this, embodiments of the present invention use the wavelet model for multiscale image decomposition and analysis as a preliminary step for the arterial pulse recovery.

Applicants have found that the finer scales can be used for the purpose of arterial pulse measurements because most of the high-frequency noise is suppressed, whereas small local heat variations produced by artery pulsation are preserved and enhanced. On the other hand, Applicants have determined that the more coarse scales of the MSD can be used for local tracking because the heat features at these scales are less affected by different sources of heat distortion (where "local tracking" involves maintaining the region of measurement at the same position on the subject's body, from frame to frame, regardless of small movements made by the subject).

Figure 7:
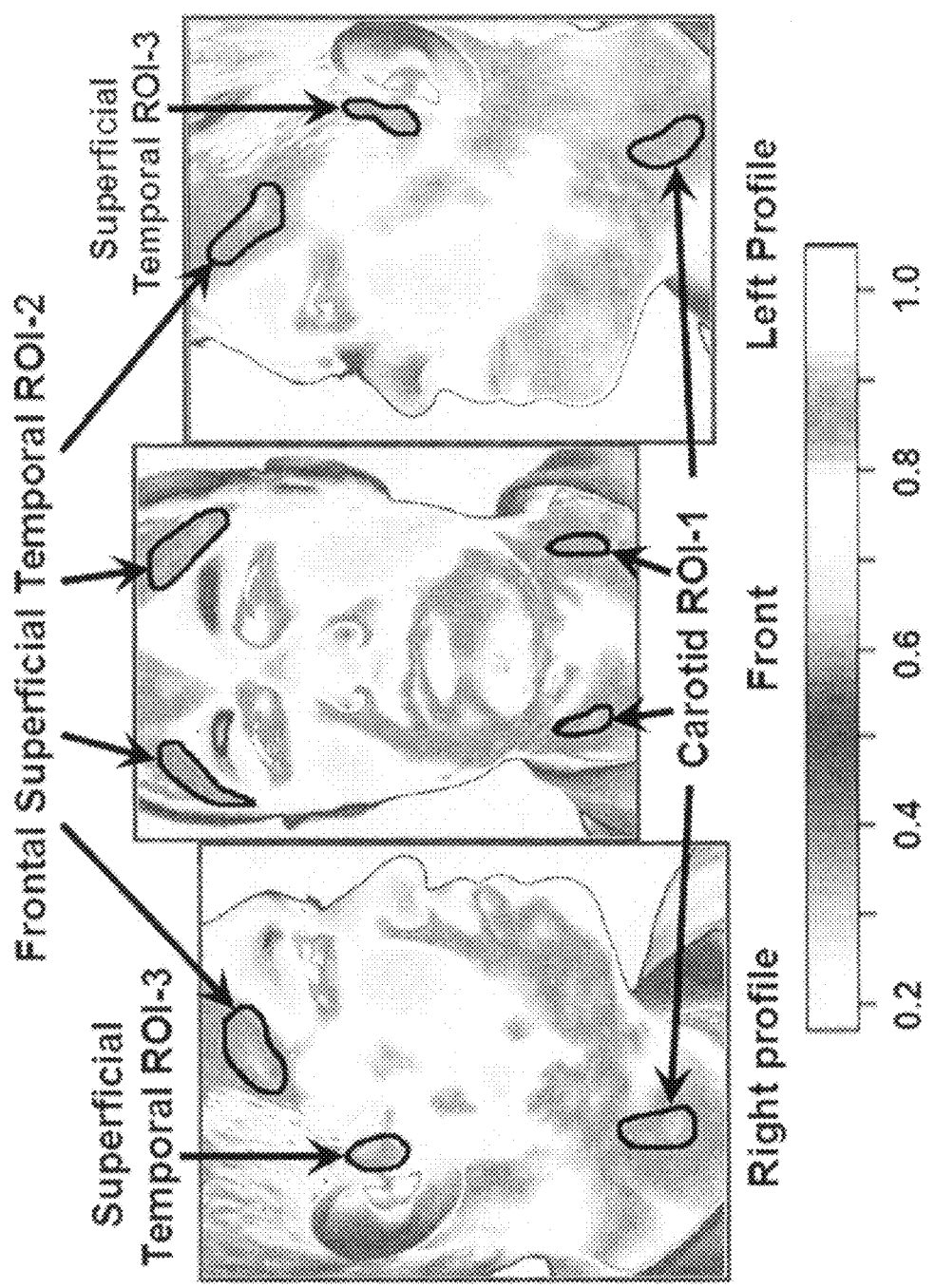
FIG. 7 shows different regions of interest (ROI) on a human face/neck for measuring arterial pulse; with a thermal image.

In the preferred embodiment, the arterial pulsation is measured from one or more of the following three different Regions Of Interest (ROI), as illustrated in FIG. 7: the main branch of the superficial temporal artery 12; the frontal superficial temporal artery 14; and/or the carotid artery 16. Although the carotid artery is a suitable ROI, the main branch of the superficial temporal artery (close to the ear) and the frontal branch are more ideally suited for the thermal-based arterial pulse measurements because they are easily accessible, contain no mucous membranes and have negligible amounts of fat and muscle tissues. Moreover, the skin in the area of the superficial temporal artery is less subject to various deformations like those observed in the carotid artery area (volumetric changes due to breathing, speech, muscle contractions, swallowing, etc).

The problem of measuring the arterial pulse is formulated in the form of registering the so-called thermal delegates of the arterial pulse propagation events along the most accessible branches of the superficial arteries. The goal is to catch those changes in thermal patterns, the delegates, which are directly linked with a sequence of arterial pulse waves propagating throughout the artery. Preferably, the longitudinal fine edges, which actually capture the intensity variation in the radial direction of the heat distribution along the artery are used to provide such delegates, as discussed below.

Figure 8:
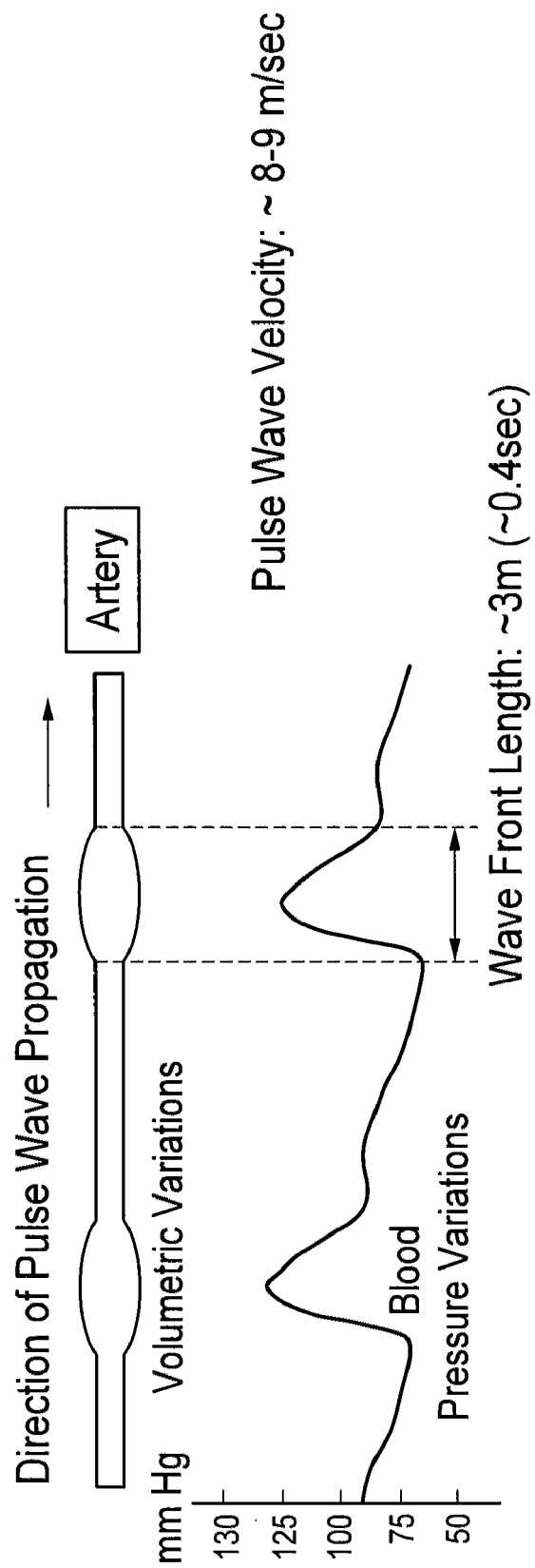
FIG. 8 shows arterial blood pressure wave propagation.

The arterial blood pressure wave is created during the ventricular systole and propagates along the arterial tree pumping the blood in the circulatory system. As shown in FIG. 8, while propagating along the arterial network, the pressure wave causes the distention of arterial walls that palpate as an arterial pulse from the major superficial arteries of the body. Generally, the aortic pulse wave velocity varies around 8.7 m/s. The shape and the speed of the arterial pulse wave changes when it propagates along the arterial tree. This is mainly because of the change in the mechanical properties of the arterial walls (elastic tapering) and the decrease of the cross-sectional areas of the arteries (geometric tapering).

Figure 9:
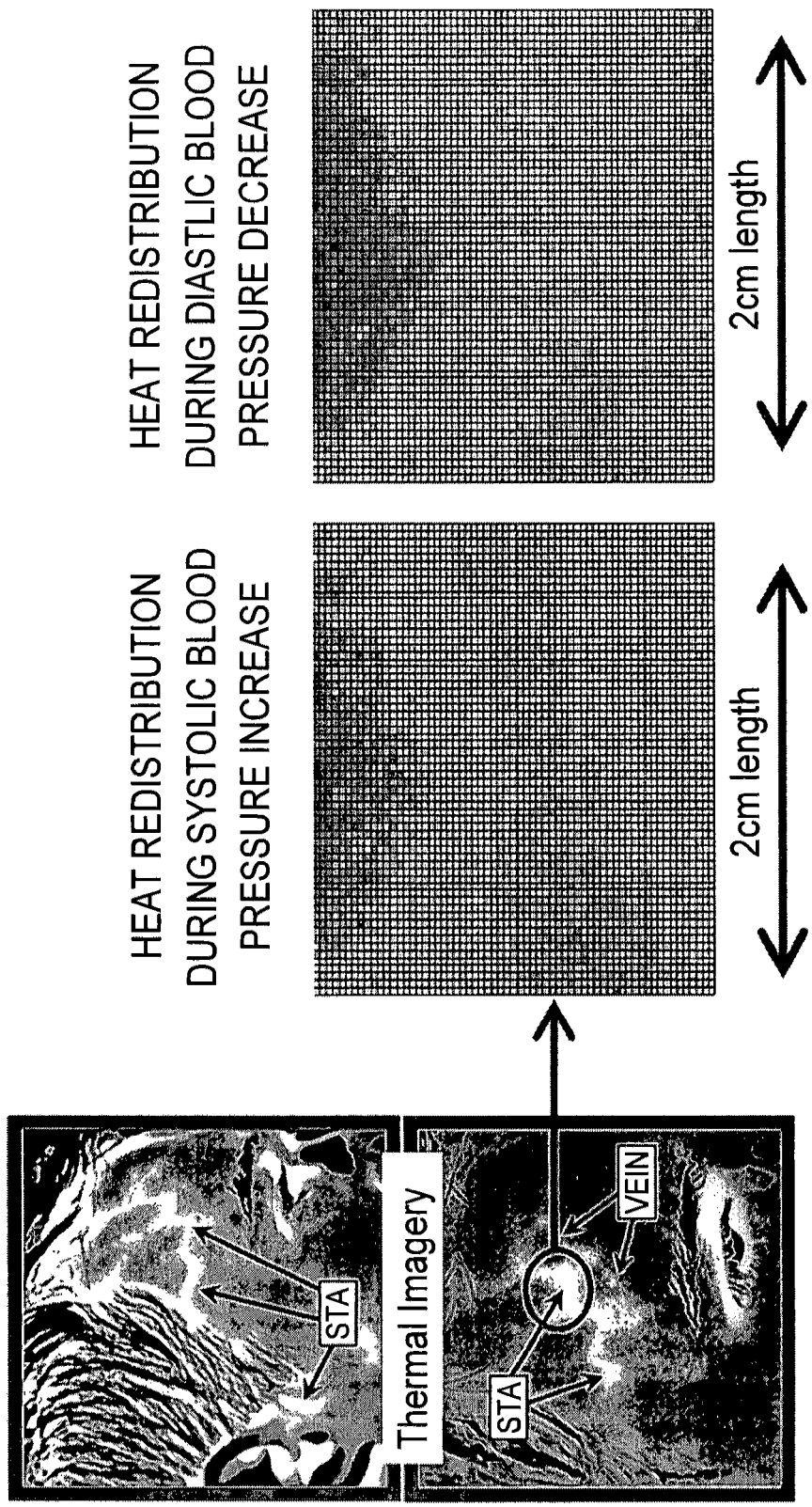
FIG. 9 is a visualization of heat redistribution during the arterial pulse propagation along a segment of a superficial artery, where heat redistribution in the radial direction perpendicular to the direction of pulse propagation is most observable. Two state of the artery are illustrated in thermal imagery: (1) Heat redistribution during the systolic blood pressure increase inside the artery; and (2) Heat redistribution during diastolic blood pressure decrease.
Figure 10:
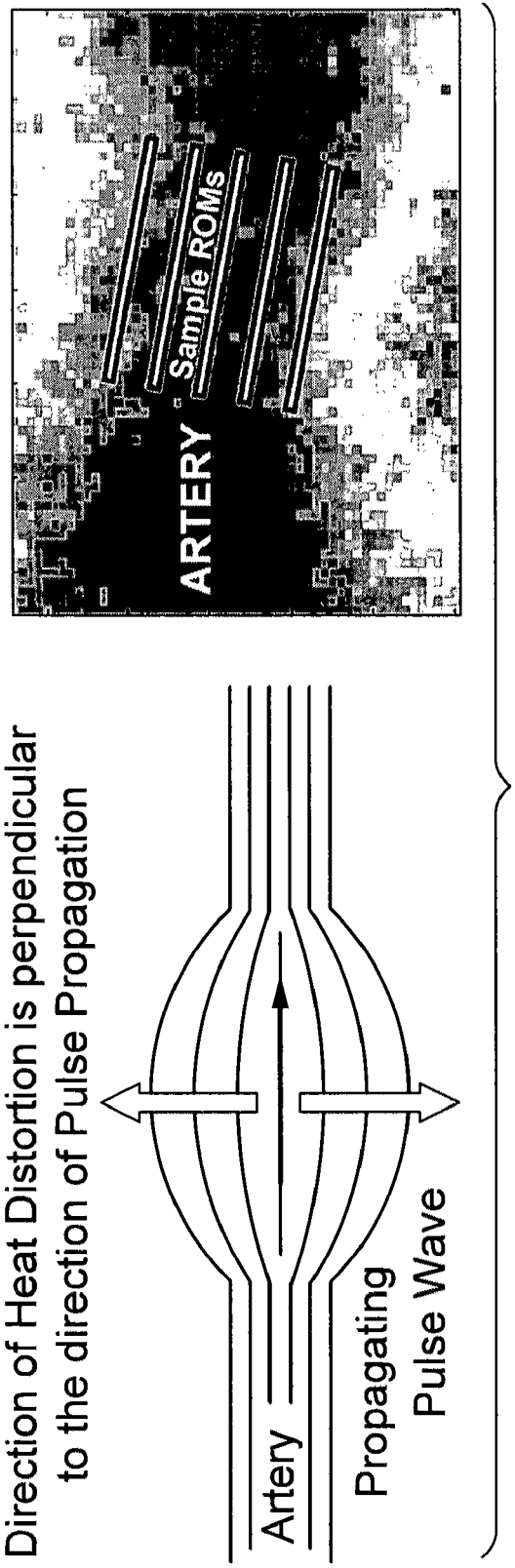
FIG. 10 shows how the direction of heat distortion in an arterial tube is perpendicular to the direction of pulse propagation, by first showing (left) a rough sketch of the differences in a thermal map along a linear segment of an arterial tube when it is dilated by an increase in blood pressure and then contracted after the pulse wave has moved forward, and then by showing (right) a thermal image of a segment of the frontal branch of the superficial temporal artery with a sample ROM configuration.

In this invention, we simply consider the arterial tree as a network of cylindrical tubes. Our hypothesis is that the arterial wall volumetric response to a pressure variation disturbs the heat distribution along the artery, as shown in FIG. 9. It is further assumed that these distortions are more pronounced in the radial, rather than longitudinal, direction. This assumption is roughly sketched in FIG. 10. The heat variations are further passed to the skin surface where they can be registered by a thermal IR camera. Since the length of the pulse wave is much longer than the length of the ROM, it is logical to catch the pulse components in some strip-like ROM oriented along the longitudinal direction of the artery (FIG. 10). In this case, the radial heat distortions caused by the pulse propagation would be in-phase at each of the ROM pixels, and their averaging at each frame would give the desired result. Unfortunately, this scheme is impractical because there is a strong contribution of irrelevant heat patterns on the skin that destroy or dramatically corrupt the arterial pulse signal. Accordingly, the ROMs are constructed in their wavelet subspaces. This way, there is a chance to separate different heat phenomena into different subspaces, and to successfully recover the signal of interest from one of the subspaces that does not overlap the others. The coarse wavelet layers should not be of interest for this purpose because the periodic arterial pulse waves do not contribute much to the overall heat changes on the skin. The prominent pulse components with respect to other patterns should reside in the horizontal (longitudinal) components of the fine wavelet layers which can be referenced as the fine edges since they encode the fine variations of the heat distribution.

Preferably, the coarse scales of MSD are used for local tracking of the ROI, whereas fine levels serve for building multiscale edges, as mentioned above. This ROI multiscale edge data is used to compute one-dimensional (1-D) arterial pulse waveforms. The Continuous Wavelet Analysis (CWA) framework and a Periodicity Detection (PD) algorithm, which is explained below, are applied to these waveforms to detect the Region of Measurement (ROM) and the final arterial pulse waveform. This ROM constitutes a small patch of skin, where the arterial heat pulsation is highly pronounced. The rationale behind the application of MSD and CWA to raw thermal data is the ability to extract the highly relevant information of the true pulsating arterial heat signal, and to remove as many noisy and irrelevant heat patterns as possible.

Figure 6A:
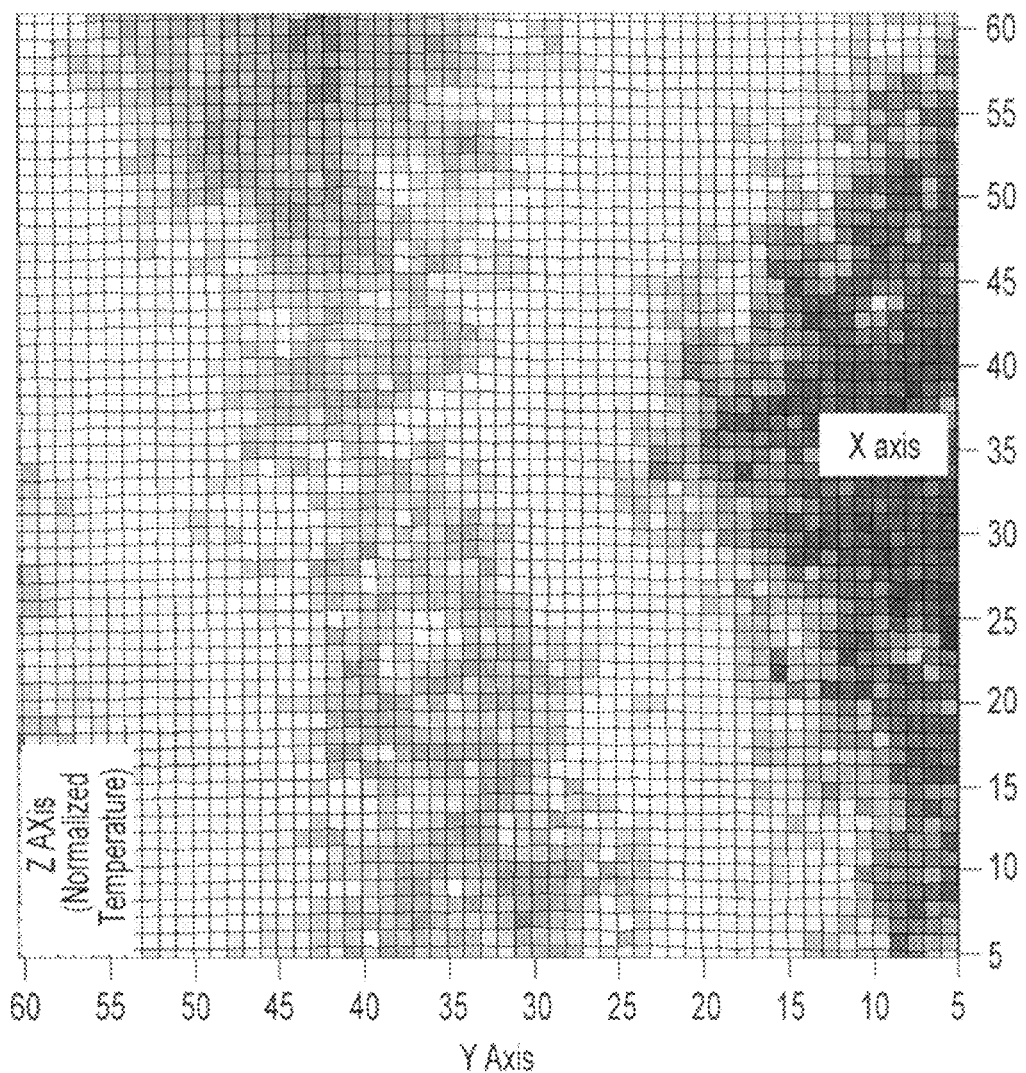
FIGS. 6(A)-6(C) illustrate the issue of thermal noise in thermal IR imaging of superficial arteries.
Figure 6B:
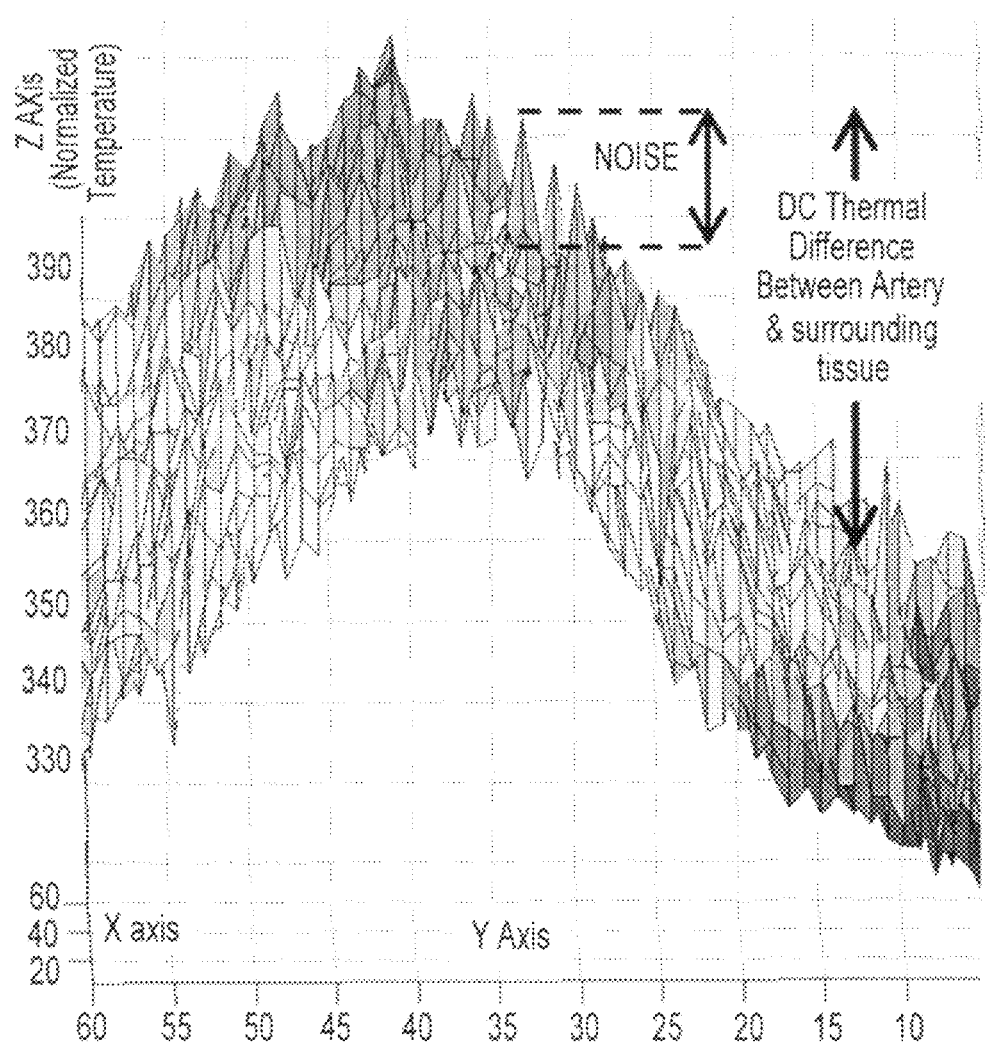
Figure 6C:
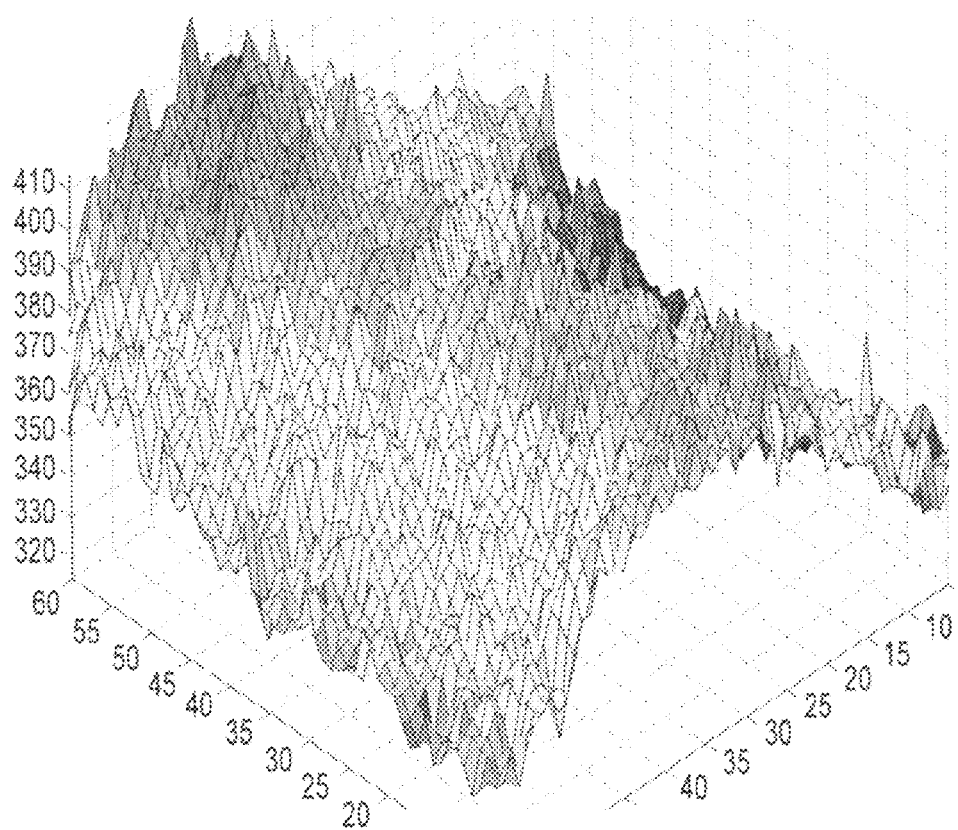

Pulsating heat contribution produced by an artery is of a very low magnitude in comparison to other heat patterns observed on the skin surface, as it is visualized in FIGS. 6(A)-6(C). To enhance the signal-to-noise ratio (where any heat variations irrelevant to the arterial pulse signal are considered to be noise), a certain configuration of ROM in terms of scale, orientation, size and location is selected to maximize the heat variations produced by the true arterial pulse, while minimizing the contribution of noisy patterns. This task is accomplished by measuring the signal-to-noise ratio in a set of experiments with different configurations of ROM. The optimal configuration of ROM/ROMs in terms of scale, orientation with respect to directional wavelet function, size and location is detected to make a measurement of the arterial pulse. As mentioned earlier, it has been found that simple averaging of the pixels within this rectangular patch does not yield a satisfactory result because heat variations due to true arterial pulsation interfere with other heat processes at such scale(s), thereby producing a corrupted arterial pulse waveform. However, this problem can be solved by splitting the filtered thermal data into orthogonal low and high scale bands using a wavelet framework, such as that disclosed in S. Mallat, "A Compact Multiresolution Representation: The Wavelet Model," Proc. IEEE Computer Society Workshop of Computer Vision, IEEE Computer Society Press, Washington DC, pp. 2-7, 1987. (hereinafter "the Mallet publication"), which is hereby incorporated by reference.

Figure 11:
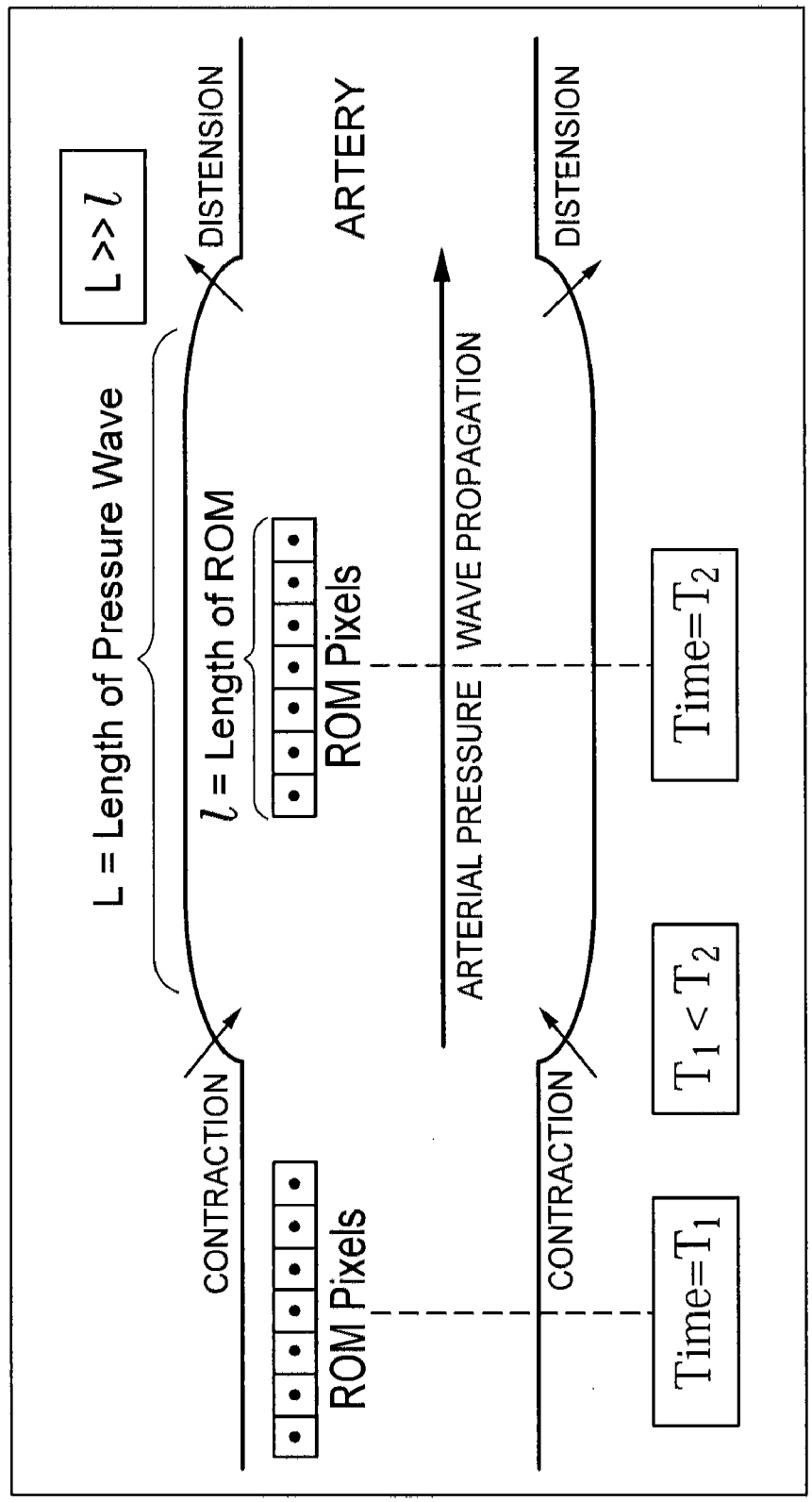
FIG. 11 shows registration of arterial pulse propagation events from the periodic distortions of fine longitudinal edges of heat distribution along an artery.

The directional wavelet filters can be applied to decompose raw thermal images at multiple scales and orientations with respect to the direction of the analyzing wavelet functions. In one embodiment, the inventors apply 2D directional Haar wavelet filters and MSD schemes such as disclosed in the Mallat publication. However, other MSD procedures that use many other filters, such as the Gabor, for example, can be successfully applied. When practicing embodiments of the invention, the choice of the MSD scheme and kernel filter will primarily affect the speed and accuracy, but conceptually the phenomena will remain the same. Currently, the inventors found the Mallat wavelet framework with the use of 2D directional Haar filters to be fast and accurate. With this approach they decompose thermal images into disjoint bands encoding Horizontal (H), Vertical (V), Diagonal (D) edges, and a residual coarse band. Depending on the image resolution, the algorithm selects a certain fine scale where the data from the wavelet sub-band that captures the radial variations in heat distribution the best is used to compute the mean value within the ROM (FIG. 11) for all frames (k) and plot it with respect to time/frame, obtaining 1-D arterial pulse waveforms. Preferably, the residual low frequency part is not included in the construction of the arterial pulse waveform. This band carries some parts of the arterial pulse signal, but in addition it also includes a significant amount of irrelevant heat information. As mentioned above, in the preferred embodiment, the wavelet components from the band/bands that encode the variations due to the effect of the arterial pulse propagation are used to compute the mean value within the ROM, such as shown in FIG. 11, which is a schematic visualization of a sample ROM configuration for certain wavelet sub-band. By ROM configuration, we mean that all frames (acquired thermal images) are processed with a certain wavelet function $\psi_{Scale}^{Direction}$ and a certain frame orientation with respect to the selected $\psi_{Scale}^{Direction}$. Other ROM configuration parameters are the ROM's topology, size and location. In FIG. 11, the ROM pixels are displayed as a one-dimensional (1D) array along the longitudinal direction of the artery. Time $T_1$ corresponds to the relaxed, undilated state of artery, and $T_2$ corresponds to the time when the artery is distended by the blood pressure increase. This causes the noticeable redistribution of heat in the radial direction. The horizontal edges shift and change the valves within the ROM. Longitudinal heat distortion due to the artery distension is not readily observable. However, since other heat processes can vary the longitudinal heat distribution, thereby corrupting the signal. In order to eliminate these corrupting heat processes, procedures are needed, to obtain a properly tuned wavelet scale, frame orientation with respect to wavelet direction, ROM size and location can yield the waveform with the best periodicity measure, as discussed below.

Detecting the Region of Measurement (ROM)

Next, the issue of detecting the ROM (Region of Measurement) within the selected ROI (Region of Interest) where the cardiac pulse signal can be measured will be discussed in more detail. The ROM is the region where the arterial pulse signal can be measured.

Experimentation has shown that the arterial pulse can be measured in a specific location close to the artery. This location depends on many anatomical parameters of an individual, such as structure of the artery and surrounding superficial veins, amount of fat, muscle tissues, etc. Usually the ROM is coincident with the point where the pulse can be palpated with a finger. The artery by itself cannot be seen in the visible spectrum, and can only barely be seen, leaving a prominent thermal imprint but with low contrast to the surrounding tissue, in LWIR (Long Wave Infra-Red). All main arteries in the human body are accompanied by a vein located in the vicinity around them. Arteries are safely located deeper inside the body and are covered by skin, muscles and fat tissues. Veins are typically located closer to the surface of skin. This is why on an LWIR spectrum arteries look colder than veins or are not seen at all. But, even though the arteries do not produce significant changes in temperature on the skin surface, they still produce a modulated temperature signal, which makes the measurement of cardiac pulse possible from the multiscale edge data.

Figure 12:
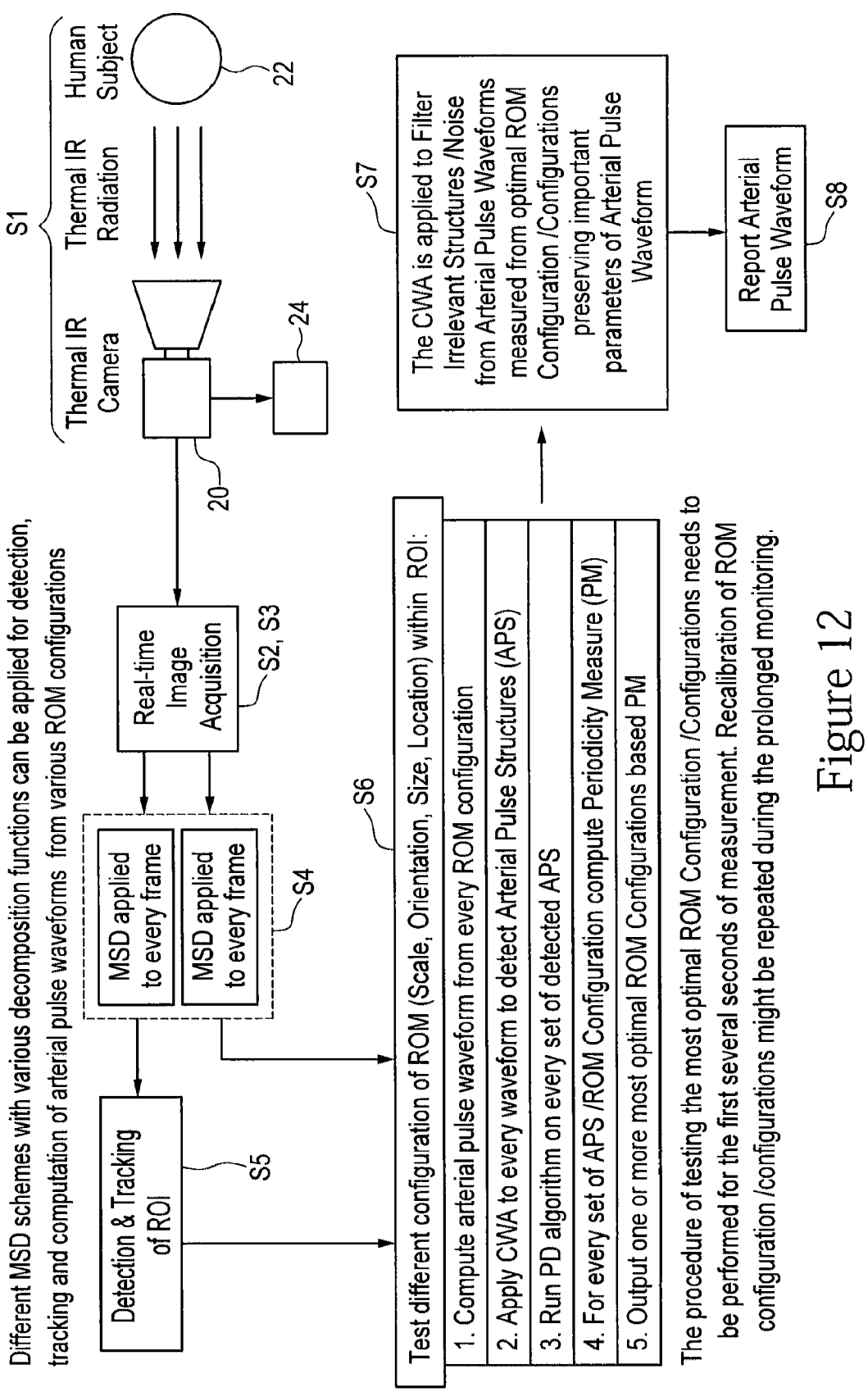
FIG. 12 is a flowchart showing the general scheme of an embodiment of the invention for measuring an arterial pulse waveform.

The next part of the process is choosing the best location for the ROM, as well as its shape within the pre-selected ROI, to measure the arterial pulse. In the preferred embodiment, this part of the process is performed in the following way, as illustrated in the flow chart of FIG. 12:

Step S1. As shown in the schematic of FIG. 12, a subject 22, such as a human patient, is positioned in a stationary manner an appropriate distance from an Infra-Red (IR) camera 20, and the camera is focused on the appropriate area of the skin. For example, the subject can be seated several feet away from the IR camera (depending on optics and camera resolution), and the IR camera is then focused on his/her face/neck. The distance from the subject to the camera is mostly determined by the optics used and the spatial resolution of the thermal IR camera. With bigger lenses (100, 150, 250 mm etc.) the distance can be significantly increased. The IR camera provides data to a computer 24, or other processing device, Step S2. Acquire N thermal images from the appropriate Observation Area (OA), such as the region containing a superficial artery that is accessible by the camera at each frame on a thermal video sequence. For off-line operation, N represents the duration of the monitoring of the arterial pulse. For example, at the frame rate of 30 frames per second, each 30 frames represent the time duration of 1 second. During real-time monitoring, N would represent the buffered data processed during a certain time. Preferably, the anatomical region monitored by the camera is an area near one of the arteries highlighted in FIG. 7: the superficial temporal artery 12; the frontal superficial temporal artery 14; and the carotid artery 16, with the superficial temporal artery 12 being the most preferred area. In general, the locations and structures of the superficial arteries are anatomically the same among the population. However some small variations from subject to subject can certainly be observed. This why the identification of proper ROM configuration is needed within the selected ROI. Such selection should preferably be done in an automatic fashion without involvement of a medical expert.

Step S3. Automatically initialize the ROI (Region of Interest) as an L×L pixel area at the center of OA. Depending on the camera resolution the parameter L is selected to cover a significant part of the field of view of the camera, with more than 25% being is preferred).

Step S4. Perform a multiscale decomposition (MSD) with appropriate decomposition scheme (Pyramid or Wavelet Decomposition) and appropriate convolution functions at each of the N frames. Multiple decomposition functions and MSD schemes can be applied, if desired.

Step S5. Use the multiple layers (coarse layers are more preferred) of the MSD to detect and track the ROI for any facial movements of the subject.

Figure 13A:
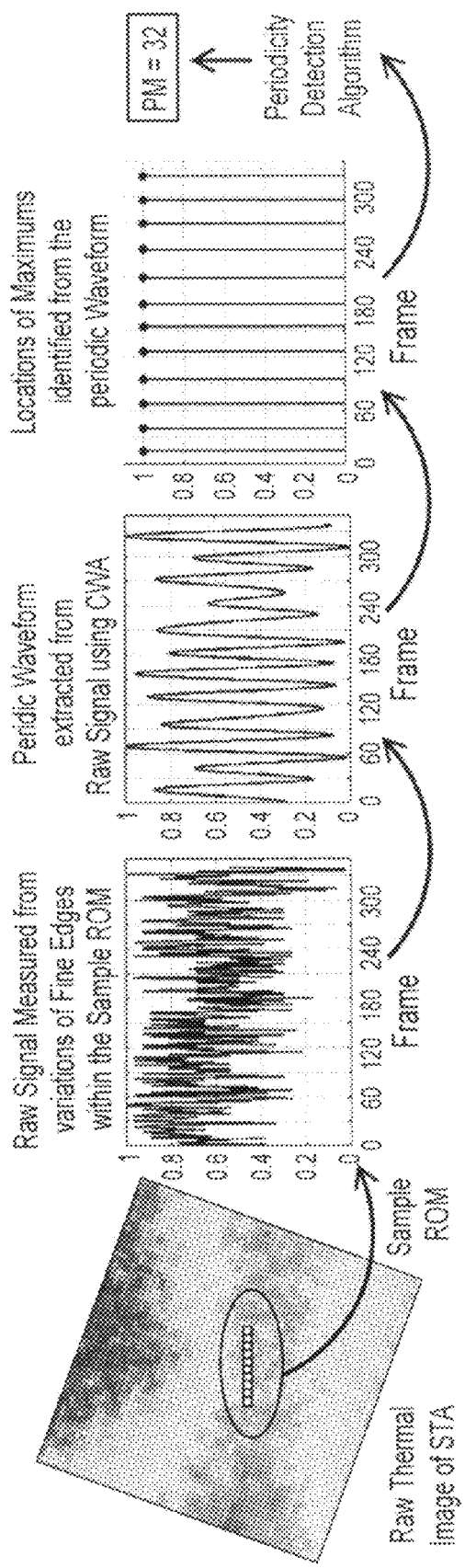
FIGS. 13(A)-13(C) show automatic detection of optimal ROM configuration (achieved by comparison of the periodicity measures for various configurations)
Figure 13B:
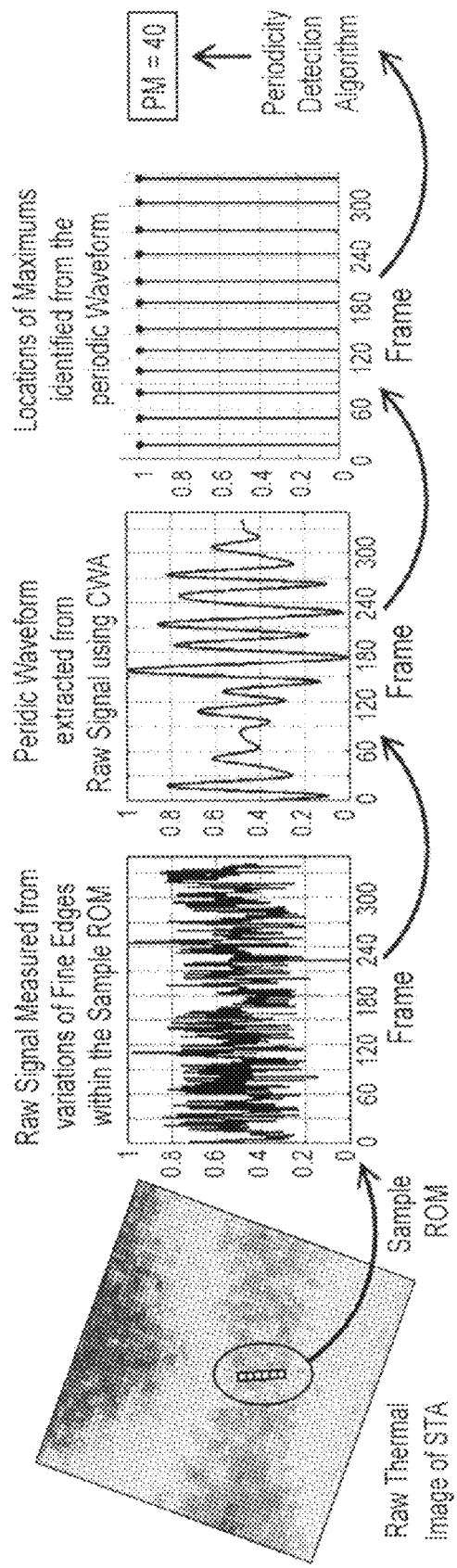
Figure 13C:
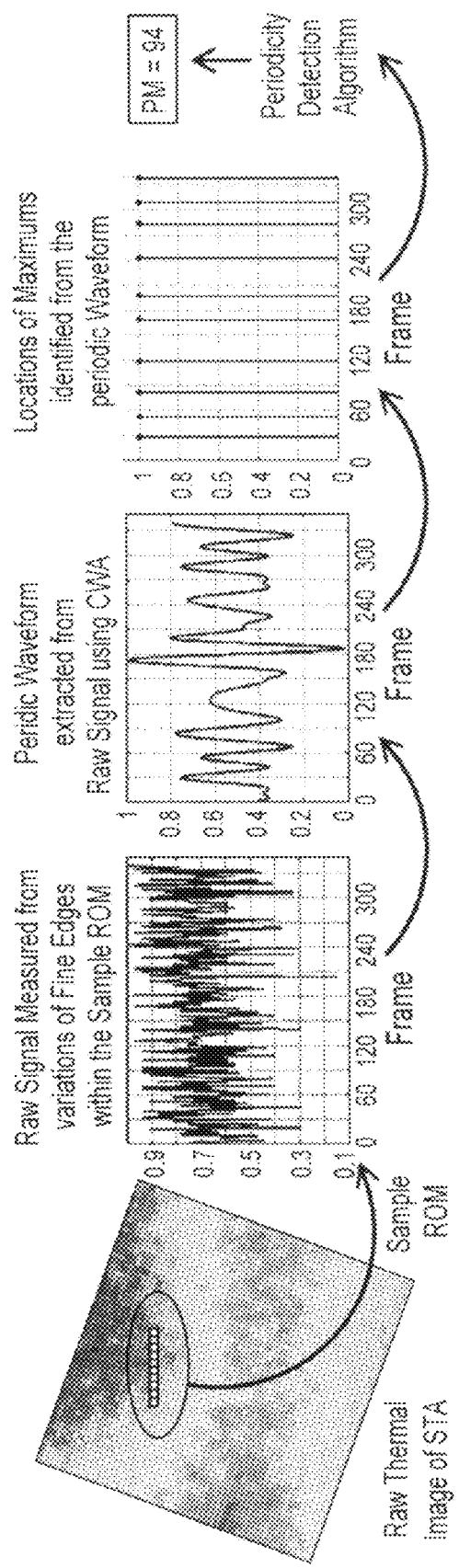

Step S6. Test different configurations of ROM (by varying parameters such as scale, orientation of the thermal image with respect to the analysis kernel function, location in the reference system of the tracked region of interest, topology of the region and its size) by comparing the Periodicity Measures (PM) computed for the arterial pulse waveforms measured from certain ROM configurations. FIGS. 13(A)-13(C) provide an example of this in which three different configurations of ROM are illustrated in the figures. The ROM configurations are schematically illustrated over the raw thermal images of the skin in the vicinity of the superficial artery. However, it should be understood that the actual measurements are performed from fine scales of the MSD pyramids. A raw arterial pulse is computed for every ROM configuration. The continuous wavelet analysis is applied next to detect the arterial pulse structures in raw arterial pulse waveforms. The time locations of the arterial pulse structures (maximums) are detected and fed into Periodicity Detection (PD) algorithm. The PD algorithm assigns a larger PM for the waveforms containing lesser amounts of the quasi-periodic arterial pulse structures. The ROM configuration that yields the optimal (smallest) PM is selected for further measurements of the arterial pulse. The procedure of testing different configurations of ROM (Scale, orientation, Size. Location) within the ROI can be summarized as follows:

1. Compute arterial pulse waveform from every ROM configuration.
2. Apply CWA (Continuous Wavelet Analysis, which is explained below) to every waveform to detect Arterial Pulse Structures (APS).
3. Run PD algorithm on every set of detected APS.
4. For every set of APS/ROM Configuration, compute the Periodicity Measure (PM).
5. Output one or more of the most optimal ROM Configurations based on the PM.

The procedure of testing the most optimal ROM Configuration/Configurations is preferably performed for the first several seconds of measurement. Recalibration of ROM configuration/configurations might be repeated during the prolonged monitoring.

Step S7. The further measurement of the arterial pulse waveform is performed from the raw thermal measurements from the ROM configuration as determined in Step S6. Arterial pulse recovery and filtering algorithm based on CWA (Continuous Wavelet Analysis, which is explained below) is applied to remove irrelevant arterial pulse structures and noise from the raw waveforms, preserving the important arterial pulse parameters and output the final Arterial Pulse Waveform (Step S8).

Continuous Wavelet Analysis (CWA)

The continuous wavelet transform (CWT) of the function $f(t)$, is defined as:

$$w(a, b) = \frac{1}{\sqrt{C_\psi}} \frac{1}{\sqrt{a}} \int_{-\infty}^{+\infty} \psi*\left(\frac{t-b}{a}\right) f(t) dt, \quad (3)$$

$$C_\psi = \int_{-\infty}^{+\infty} \frac{|\psi(\omega)|^2}{|\omega|} d\omega < \infty \quad (4)$$

$$\Psi(\omega) = \int_{-\infty}^{+\infty} \psi(t) e^{-i\omega t} dt \quad (5)$$

The self-similar functions $\psi(t)$ have to be oscillating functions bounded at the origin, and represent an orthonormal basis. If the integrals in equations (3)-(4) are bounded, then there exists an inverse continuous wavelet transform (ICWT), which gives us the reconstructed signal:

$$f(t) = \langle f(t) \rangle + \frac{1}{\sqrt{C_\psi}} \frac{1}{a^2} \int_a \int_b w(a, b) \psi\left(\frac{t-b}{a}\right) db\, da \quad (6)$$

Preferably, using the Mexican Hat (MH) wavelet (other wavelet functions can also be applied, such as the well-known morlet wavelet function, for example), characterized by its good localization in the spatial domain, the local minima and maxima of the arterial pulse can be isolated. In the preferred embodiment, the CWA framework is applied to solve two tasks: to automatically detect local CWT arterial pulse structures (maximums) in the ROM identification procedure, and to filter the final cardiac waveform from the noise, leaving the important signal structure as unchanged as possible. Assuming that the arterial pulse is a quasi-periodic signal within a short period of time, this assumption makes the automatic detection of the ROM possible when the Periodicity Detection (PD) algorithm, explained below, is applied.

Figure 14:
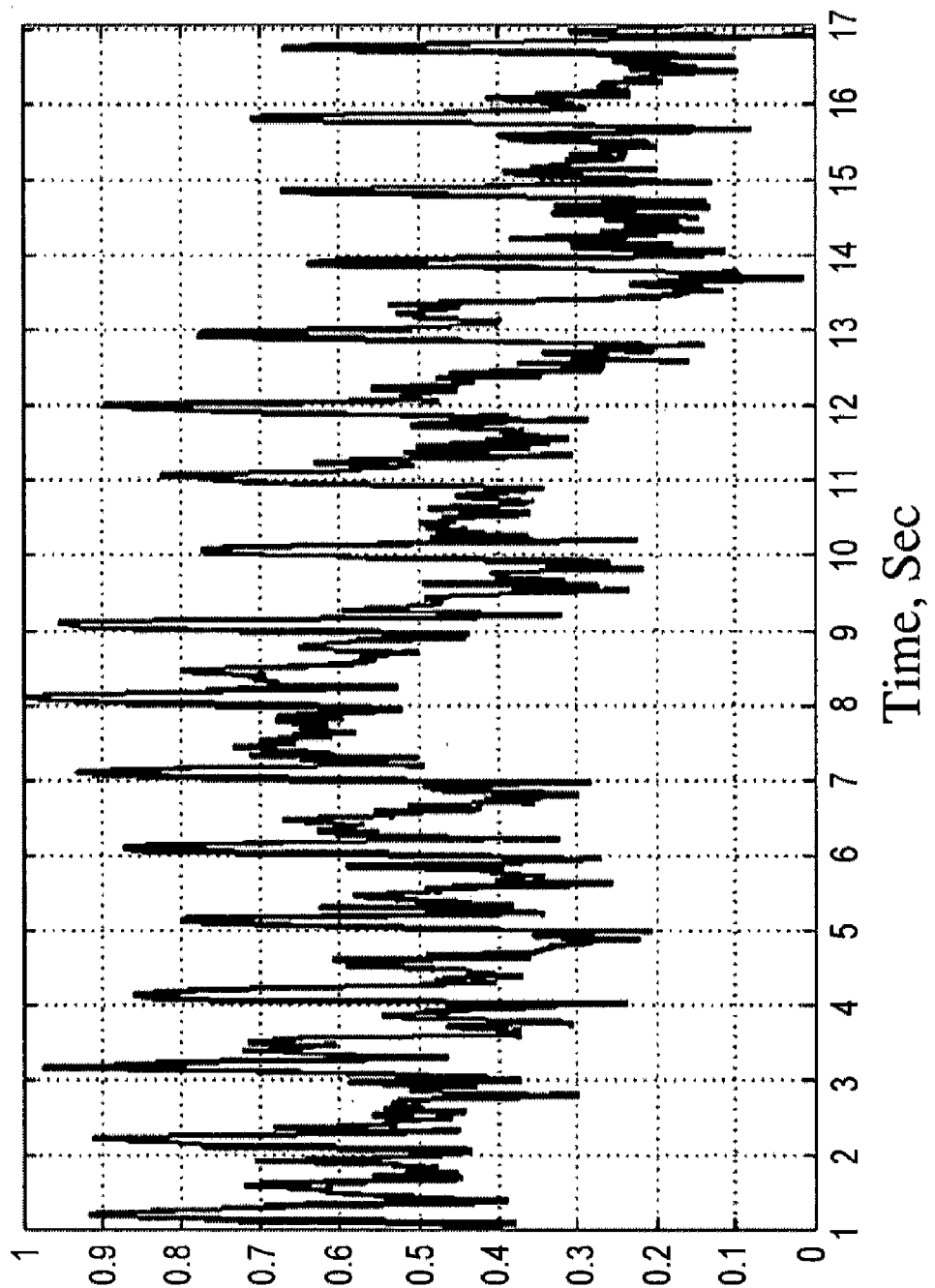
FIG. 14 is a graph of the raw thermal profile of an arterial pulse as measured from the carotid artery.

An example of a typical arterial pulse waveform measured from the carotid artery region with the approach described herein is shown in FIG. 14. A six second fragment of the arterial pulse and corresponding CWT (Continuous Wavelet Transform) plane are illustrated in FIG. 15. From the plot, one can see high-frequency, low-power noise concentrated at small scales (fine details) region of the CWT plane. One can also notice that those structures which continue from the fine to coarse resolution region on the CWT plane are related to the true arterial pulse peaks. The strategy is to remove the noise from the signal without disturbing important structures. Therefore, by removing (i.e., setting to zero) those structures from the CWT plane that begin at a fine resolution region but do not have continuation toward the coarse scales, these structures just degrade to zero at some intermediate scale. This approach is reasonably supported, since the true arterial pulse waveform observed in blood pressure waves are sharp peaks which slowly come into the wide support at the DC level of the pressure waveform. The result of such a filtering procedure can be seen in FIG. 16(B), where one can see that only the meaningful structures remain. Then, applying the inverse continuous wavelet transform (ICWT) of Equation (6), results in a reconstructed signal as illustrated in FIG. 16(A). From FIG. 13(A), one can even observe the time location of such important events in the cardiac cycle as: (a) systolic peak pressure; (b) dicrotic notch; and (c) the end-diastolic pressure temperature profile.

Figure 17:
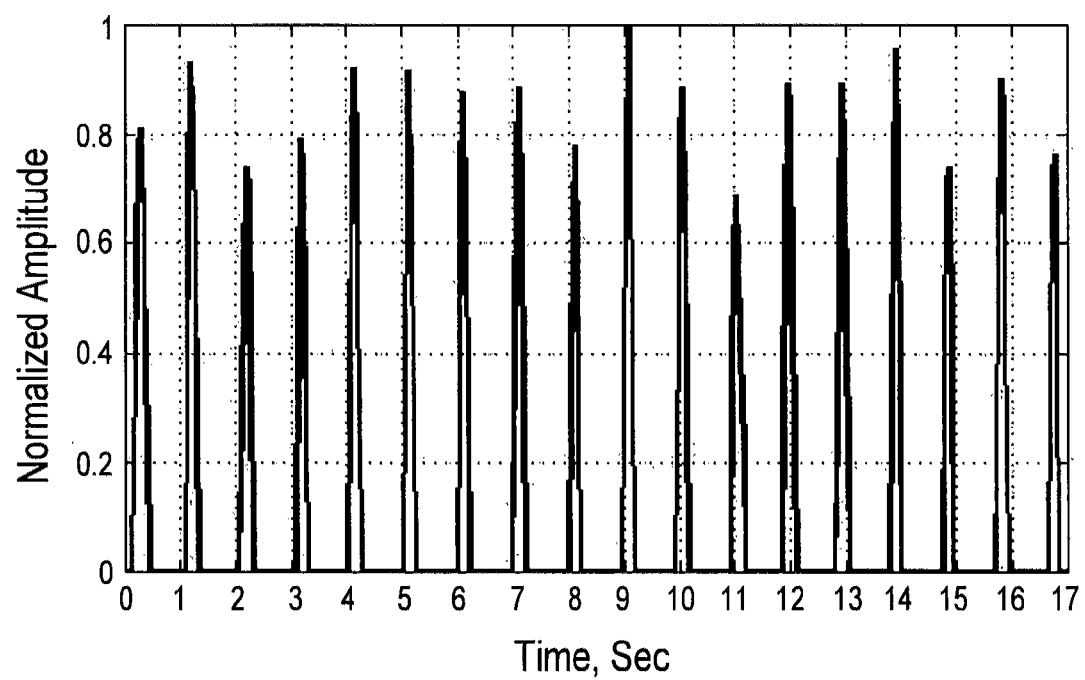
FIG. 17 is a reconstructed arterial pulse waveform from a carotid artery, obtained by CWT filtering and thresholding (only containing the cardiac frequency content)

Turning now to FIG. 17, this figure demonstrates a reconstructed signal after removing noisy structures from the CWT plane, followed by thresholding. Thresholding removes the structures that are significantly lower in power than the systolic pressure peaks. This final waveform shows the exact locations of the systolic peaks which represent the cardiac rhythm information, beat to beat information and information heart rate variability. The maxima extracted from this waveform are fed to the Periodicity Detection (PD) algorithm discussed below.

Applying the inverse continuous wavelet transform we do not attempt to recover a particular harmonic, as is done in the Fourier Transform based filtering techniques. Actually, we recover the structures belonging to a particular scale. Their time behavior is not restricted to a particular spacing rate.

This makes the present approach quite valuable in dynamic, real-life applications where the momentary changes in the heart rate and heart rate variability are of particular importance.

Periodicity Detection (PD) Algorithm

Next, the PD algorithm that is used for automatic selection of the optimal ROM (Region of Measurement) configuration will be discussed. The intention of the algorithm is to find out the way to assign larger values, the PM, for the waveforms which contain lesser amounts of the quasi-periodic arterial pulse structures similar to those in actual arterial pulse data. The algorithm presented below labels the waveforms with appropriate PMs, according to their periodicity content. The algorithm may utilize different statistics and schemes to identify the most reliable waveform in terms of periodicity and relevance to the actual arterial pulse. The algorithm can be summarized as follows:

Input: a set of N local maxima detected with CWA from 1-D arterial pulse waveforms as explained above and in FIGS. 13 (A-C). In other words, use the maximum at time $t_1$ (Max $[t_1]$), the maximum at time $t_2$ (Max $[t_2]$), etc., until reaching $t_N$ (Max $[t_N]$).

Begin:
→Compute the average distance between two maxima:

$$L=(t_N-t_1)/(N-1)$$

→Set: PM=0, i=0
→do i←i+1

$$L_i=(t_{i+1}-t)$$

$$PM=PM+|L-L_i|$$

until i=N−1
Output: PM(Periodicity Measure)

The version of the periodicity detection algorithm presented above assigns bigger periodicity measures for the waveforms containing a lesser amount of quasi-periodic arterial pulse structures. Those sets of arterial pulse structures in which temporal behavior is more similar the real behavior of the arterial pulse propagation events along an artery are assigned with smaller periodicity measure values.

The Periodicity Detection algorithm can vary in its architecture, for example, such as the output of the algorithm could be a vector, a matrix or even a tensor of periodicity measures describing the intrinsic features of measured arterial pulse waveforms in a sense of their relevance to the true arterial pulse propagation phenomena in the circulatory system.

More types of confidence scores can be designed in the future for the same purpose as described above: to characterize every computed raw arterial pulse waveform with a certain degree of relevance to the quasi-periodic nature of the arterial pulse propagation phenomena.

Local Tracking and Multi-Scale Edges

The present method is preferably either performed in a controlled environment or with the use of a global tracker that tracks significant movements of the subject to trigger a position change of the camera to keep the subject (such as a human face) in the field of view of the camera. But, even with a high level of subject cooperation, or with state-of the art global trackers applied, there are still small uncontrolled local motions and deformations due to muscle contraction, spontaneous body movements, breathing, heartbeat, and so on. These small movements may dramatically affect the shape of the measured signal and make it impossible to get any meaningful waveforms without a robust local tracking method.

The main problem in accurate local tracking of ROI (Region of Interest) in thermal IR is the choice of tracking features. These features need to be invariant to any temperature affecting phenomena, like sweating, blushing, touching, external heat radiation, air flow, arterial pulse propagation etc. Experiments have suggested using coarse scale representations (coarse edges, rather than fine edges which are quite variant and in fact are used for computation of the arterial pulse) obtained with MSD procedure (different decomposition kernels and decomposition schemes can be applied) to avoid most of the unwanted thermal distortions. At these coarse representations, high contrast (with respect to surrounding structures), local maxima (so-called fiducial marker points) are selected to serve as tracking features. By matching the local maxima (fiducial points) from frame to frame, the reference system for the ROI is tracked at each thermal frame. All of the coordinates of the ROM are recomputed at each frame in this reference system automatically.

Details of the Experimental Setup

The sensor used in the experiments is a long-wave Phoenix IR camera from FLIR with a thermal sensitivity less than 0.035 C. Of course, the specific sensor used in the experiments is only an example of one suitable type of sensor, and other types of sensors are also contemplated as being within the scope of the invention. Similarly, the specific settings and other details of the experiments are also provided as suggestions only, and other settings, etc. may also be used. The image sequences captured by the camera had a 14-bit extended dynamic range in a 320×256 format. The video frames were acquired at a rate of approximately 30 frames per second (fps). Higher frame rates of up to 200 fps are currently available in state-of-the art thermal IR imaging cameras, and can be used in demanding applications if needed. As a baseline for the arterial pulse measurements, a multi-parameter vital signs monitor from Smiths Medical was used. The oximetry sensor was attached to record the peripheral pulse waveforms which served as the ground-truth data in experiments. The thermal and ground-truth data acquisition was synchronized to observe the correlation between the two modalities.

Experimental Results and Discussion

Figure 18A:
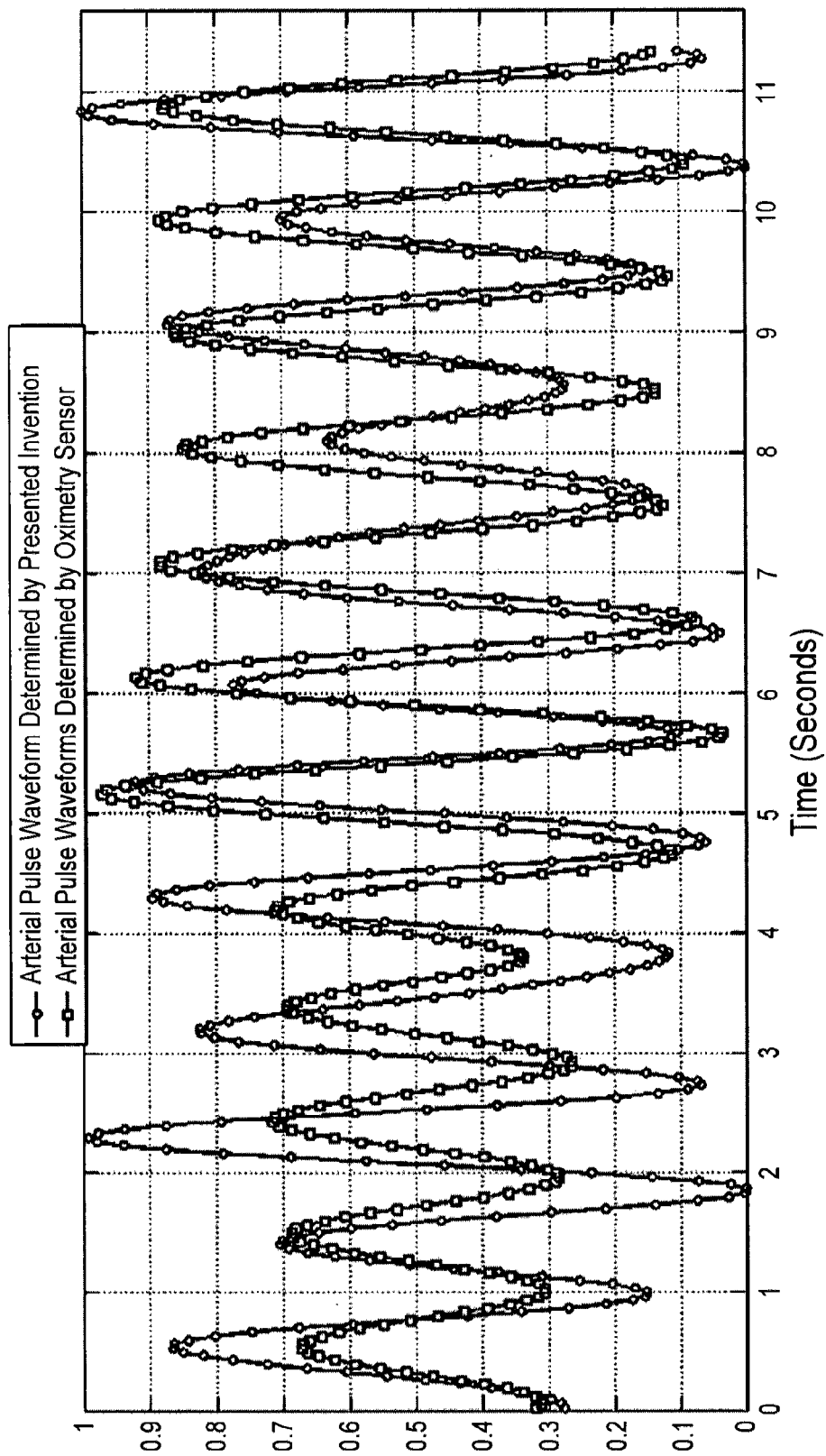
FIGS. 18(A) and 18(B) show the experimental results from one of the subjects tested.
Figure 18B:
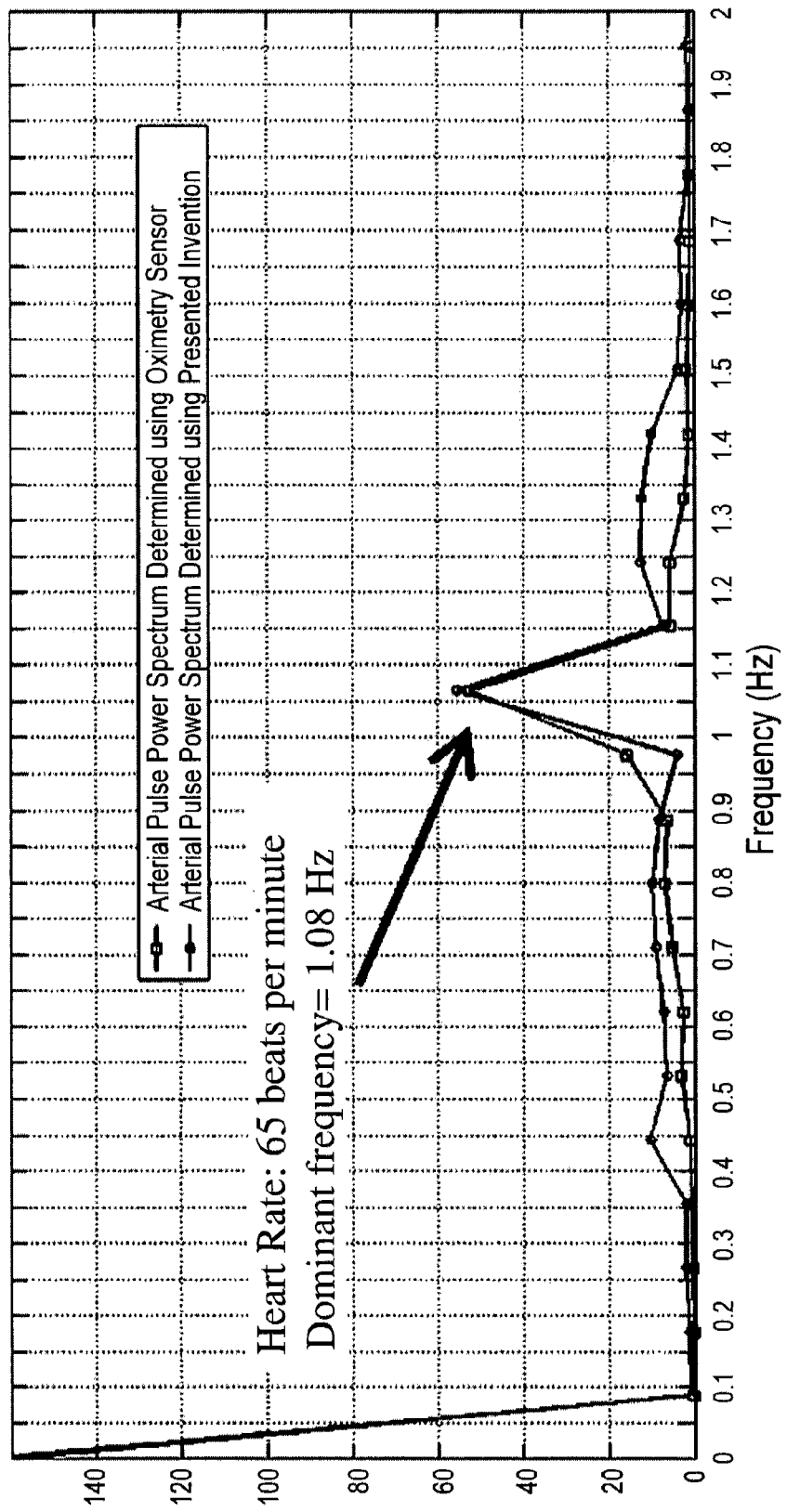

Eight subjects (seven males and one female) with ages in the range of 25-45 years old participated in our study consistent with IRB approval. Each subject was seated on a chair that was placed between one and four feet away from the camera. The acquisition time for the arterial pulse measurement was between twenty and forty seconds, with a frame rate of 30 frames per second (fps). The oximetry sensor was attached to record the peripheral pulse waveforms, which are referenced as the ground-truth data. The thermal and ground-truth data acquisition was synchronized to observe the correlation between the two modalities. The results of the arterial pulse measurements for one of the eight subjects are presented in FIGS. 18(A) and 18(B). The 12-seconds arterial pulse waveforms measured from the thermal IR data are plotted with the simple lines, and the corresponding ground-truth data are plotted with the lines that include squares. The frequency content of the waveforms is given underneath the arterial pulse waveforms plot. Since the subjects were relaxed and did not have heart conditions, all of the heartbeats appeared equally spaced in the time domain, and the corresponding power spectrum has one dominant frequency component associated with the heart rate (the strong peak at zero frequency relates to the DC component of both the ground-truth and thermal based arterial pulse waveforms). In all eight cases, the inventors obtained perfect correlation between the thermal-based and the ground-truth (oximetry) pulse data with a perfect match to heart rate.

Based on the experimental results, one can conclude that that the arterial pulse propagation causes measurable periodic distortions of the fine horizontal edges of the heat distribution along the artery. The idea of MSD processing of the raw thermal images with the intention to identify the decomposition layer which encodes most of the heat variations produced by the arterial pulse propagation is one of the important contributions of several embodiments of the present invention. Another important conceptual and practical contribution was the designing of an approach for automatic identification of the configuration for the region of measurement (ROM) of the arterial pulse in terms decomposition scale, orientation of thermal image with respect to analyzing decomposition function, region topology, size and location with a certain region of interest such as the temporal one. The periodicity detection algorithm is the part of this concept that makes use of the periodic nature of the events of the arterial pulse propagation to make a proper selection of ROM configuration. The other part of the automatic ROM configuration detection framework is the filtering algorithm based on the continuous wavelet analysis, which selectively removes the irrelevant structures and noise from 1D arterial pulse waveforms measured from a certain ROM configuration. The algorithm is capable of robustly identifying the locations of the arterial pulse structures which are fed into the periodicity detection algorithm.

One strength of the invented method is the capability to measure the interbeat intervals, instead of just the estimation of the heart rate frequency. Accurate monitoring of heart rate and heart rate variability in both time and frequency domains is important in medical testing of cardiovascular and autonomic regulatory functions, estimation of mental and emotional loads, assessment of health in general. The presented device can potentially find numerous applications in the fields where the non-contact and non-intrusive monitoring of heart rate and its variability are needed.

One of the great advantages of the approach described above is the use of mathematical statistics and information theory for robust measurement of the arterial pulse waveforms. After the preliminary steps of identification of several ROM configurations are complete, there is an issue of how to faithfully fuse the information relevant to arterial pulse from these ROM configurations into one enhanced signal. The goal is to recover the most complete and accurate final waveform, without corrupting it by improper fusion schemes. The present inventors approach this issue through the use of mathematical statistics and information theory. In the present approach, the information from multiple sources/channels, such as the ROM configurations is boosted by the fusion through Bayesian statistics and statistical learning methods (Kittler, J., Hatef, M., Duin, R. P. W., and Matas, J., "On Combining Classifiers", *IEEE Transactions on Pattern Analysis and Machine Intellegence*, Vol. 20, No. 3. 1998), which is hereby incorporated by reference. On each input channel the classification decision toward the relevance of the measured waveform to the actual phenomena of the arterial pulse propagation is used to compute the likelihood that the information observed through a certain channel belongs to an instance of the arterial pulse wave. The preference (higher weights) are given to the channels for which the observed data yields the highest probability. The other channels contribute to the final signal with lesser weights. The classification method is based on the statistical learning approach, called AdaBoost: Y. Freund and R. E. Schapire, "A decision-theoretic generalization of online learning and an application to boosting," In *Computational Learning Theory* (*Eurocolt*), 1995, which is hereby incorporated by reference. The features learned by AdaBoost come from the entropy measures and periodicity patterns extracted from observed information of multiple data channels. In very general definition, the entropy describes the level of disorder, or in other words the measure of chaos in a system, which is the analyzing arterial pulse signal in the present method. The current inventor's approach makes use of the entropy to represent the measured signals in the format suitable for the AdaBoost classifier. Some basic definitions and sample analysis on how the entropy is applied in information theory can be found in Kinsner, W., "Is entropy suitable to characterize data and signals for cognitive informatics?" Cognitive Informatics, 2004. Proceedings of the Third IEEE International Conference on 16-17 August 2004 Page(s): 6-21, which is hereby incorporated by reference.

Some potential applications of this work are in the field of non-contact health state/physiology monitoring, medical diagnostics and predication of various dangerous health conditions (such approaching heart attack, stroke, physical and mental stress etc.), smart rooms, human-computer interaction, polygraph testing and intent identification. Of course, other applications are also considered as being within the scope of the invention.

While various embodiments of the present invention have been shown and described, it should be understood that other modifications, substitutions and alternatives may be apparent to one of ordinary skill in the art. Such modifications, substitutions and alternatives can be made without departing from the spirit and scope of the invention, which should be determined from the appended claims.

Various features of the invention are set forth in the appended claims.

What is claimed is:

1. A method for measuring of arterial pulse comprising steps of obtaining a sequence of thermal infrared images;

performing a first analysis of said sequence of obtained thermal infrared images to detect at least one region of interest for further analysis;

performing a second analysis of said sequence of obtained thermal infrared images to track said at least one region of interest, wherein said second analysis includes detecting a corresponding spatial location of each of said at least one region of interest;

performing a third analysis of said at least one region of interest to select at least one configuration of a region of measurement of arterial pulse within said corresponding region of interest; and determining, using a processor, at least one arterial pulse waveform from said selected configuration of region of measurement.

2. The method according to claim 1, wherein said first analysis includes automatic selection of a pixel area using multiscale image decomposition and multiresolution analysis.

3. The method according to claim 2, wherein:

said multiscale decomposition analysis includes at least one of the following: Laplacian pyramid structures, Gaussian pyramid structures, Gradient Pyramid structures, ratio-of-low pass pyramid structures and wavelet decomposition schemes; and said multiresolution analysis includes application of convolution filters to determine said at least one region of interest.

4. The method according to claim 1, wherein said second analysis automatically tracks said at least one region of interest on every thermal infrared image using at least one of the following: Laplacian pyramid structures, Gaussian pyramid structures, gradient pyramid structures, ratio-of-low pass pyramid structures and wavelet decomposition schemes; and said multiresolution analysis includes application of convolution filters to determine salient, robust and permanent features for tracking of said region of interest.

5. The method according to claim 1, wherein said second analysis automatically tracks said at least one region of interest on every thermal infrared image using at least one of the following: Laplacian pyramid structures, Gaussian pyramid structures, gradient pyramid structures, ratio-of-low pass pyramid structures and wavelet decomposition schemes; and
said multiresolution analysis includes application of convolution filters for identification and configurations of said region of measurement.

6. The method according to claim 1, wherein said second analysis automatically tracks said at least one region of interest on every thermal infrared image using at least one of the following: Laplacian pyramid structures, Gaussian pyramid structures, gradient pyramid structures, ratio-of-low pass pyramid structures and wavelet decomposition schemes; and
said multiresolution analysis includes application of convolution filters for identification of arterial pulse structures in measurement of arterial pulse waveforms.

7. The method according to claim 1, wherein said second analysis automatically tracks said at least one region of interest on every thermal infrared image using at least one of the following: Laplacian pyramid structures, Gaussian pyramid structures, gradient pyramid structures, ratio-of-low pass pyramid structures and wavelet decomposition schemes; and
said multiresolution analysis includes application of convolution filters for determining periodicity measures for the arterial pulse waveforms measured from a plurality of said configurations.

8. The method according to claim 1, wherein said second analysis automatically tracks said at least one region of interest on every thermal infrared image using at least one of the following: Laplacian pyramid structures, Gaussian pyramid structures, gradient pyramid structures, ratio-of-low pass pyramid structures and wavelet decomposition schemes; and
said multiresolution analysis includes application of convolution filters for filtering the arterial pulse waveforms to minimize noise and data irrelevant to arterial pulse structures.

9. The method according to claim 1, wherein said second analysis automatically tracks said at least one region of interest on every thermal infrared image using at least one of the following: Laplacian pyramid structures, Gaussian pyramid structures, gradient pyramid structures, ratio-of-low pass pyramid structures and wavelet decomposition schemes; and
said multiresolution analysis includes application of convolution filters for accurate localization of arterial pulse peaks within the arterial pulse waveform.

10. The method according to claim 1, wherein said second analysis automatically tracks said at least one region of interest on every thermal infrared image to establish a spatial location of said at least one region of interest on every frame.

11. The method according to claim 1, wherein said second analysis comprises:
making use of a global and local tracker to perform a robust tracking of said at least one region of interest.

12. The method according to claim 1, wherein said third analysis automatically identifies said at least one configuration of a region of measurement of the arterial pulse using quasi-periodic nature of the arterial pulse.

13. The method according to claim 1, wherein said at least one region of interest is a region in a vicinity of major superficial arteries of a subject.

14. The method according to claim 13, wherein said region of interest corresponds to one of the following: a superficial temporal artery, a frontal branch of a superficial temporal artery, a carotid artery, a radial artery of an arm and a brachial artery of an arm.

15. The method according to claim 1, wherein said third analysis comprises:
performing at least one multiscale decomposition with at least one appropriate decomposition function at each frame of said thermal infrared images;
constructing various configurations of said region of measurement in terms of at least one of scale, orientation, size and location, within limits of said at least one tracked region of interest;
computing the arterial pulse waveform from every said region of measurement configuration;
applying continuous wavelet analysis to every said arterial pulse waveform to detect arterial pulse structures;
running a periodicity detection algorithm on every set of said detected arterial pulse structures;
computing a periodicity measure for every said set of detected arterial pulse structures; and
selecting and outputting at least one optimal region of measurement configurations based on said computed periodicity measure.

16. The method according to claim 1, wherein said third analysis comprises:
performing analysis of said sequence of obtained thermal infrared images to identify heat patterns which are triggered by effects of arterial pulse propagation;
computing raw arterial pulse waveforms from a plurality of configurations of said region of measurement based on at least one of: scale, orientation, topology, size, location;
estimate a confidence score for every computed raw arterial pulse waveform, where said confidence score represents a certain degree of relevance to pulsatile nature of arterial pulse phenomena;
identifying at least one appropriate configuration of region of measurement based on comparing said estimated confidence scores for every configuration of region of measurement;
outputting one or more of said appropriate configurations of region of measurement for determining the arterial pulse.

17. The method according to claim 1, further comprising a step of measuring and imaging the thermal infrared energy naturally radiated from a subject, without projecting any kind of energy to said subject.

18. The method according to claim 1, wherein said step of determining an arterial pulse waveform determines the arterial pulse waveform based on measurement of thermal variations caused by arterial blood pressure wave propagation.

19. A method for measuring of arterial pulse comprising steps of
obtaining a sequence of thermal infrared images;
decomposing the sequence of thermal infrared images into a set of fine and coarse scaled measurements, wherein the coarse scaled set is scaled at a resolution to identify heat changes in skin temperature and exclude fine variations of heat distribution attributed to arterial pulse waves and the fine scaled set is scaled at a resolution to identify fine variations in heat distribution attributed to arterial pulse waves;
identifying and tracking a region of interest with from the coarse scaled set; and determining, using a processor, at least an arterial pulse waveform from the fine scaled set by building multi scale edge data and computing the arterial pulse waveform.

20. The method according to claim 19, wherein said decomposing comprises applying directional wavelet filters to thermal image data of the sequence of thermal images.

21. The method according to claim 20, wherein said applying direction wavelet filters decomposes the thermal images into disjoint bands encoding horizontal, vertical, diagonal edges, and a residual coarse band, and said determining determines pulse components from the horizontal band.

* * * * *

UNITED STATES PATENT AND TRADEMARK OFFICE
CERTIFICATE OF CORRECTION

PATENT NO. : 8,360,986 B2
APPLICATION NO. : 11/824665
DATED : January 29, 2013
INVENTOR(S) : Farag et al.

Page 1 of 1

It is certified that error appears in the above-identified patent and that said Letters Patent is hereby corrected as shown below:

In the Specification:

Col. 5, line 18     After "namely" please delete "that".

Signed and Sealed this
Thirtieth Day of July, 2013

Teresa Stanek Rea
*Acting Director of the United States Patent and Trademark Office*